United States Patent
Donsante et al.

(10) Patent No.: US 12,070,510 B2
(45) Date of Patent: Aug. 27, 2024

(54) INJECTION OF SINGLE-STRANDED OR SELF-COMPLEMENTARY ADENO-ASSOCIATED VIRUS 9 INTO THE CEREBROSPINAL FLUID

(71) Applicants: Emory University, Atlanta, GA (US); REGENXBIO Inc., Rockville, MD (US)

(72) Inventors: Anthony Donsante, Decatur, GA (US); Karen Kozarsky, Bala Cynwyd, PA (US); Nicholas Matthew Boulis, Atlanta, GA (US); Jonathan Patrick Riley, Williamsville, NY (US)

(73) Assignees: Emory University, Atlanta, GA (US); REGENXBIO. Inc., Rockville, MD (US)

( * ) Notice: Subject to any disclaimer, the term of this patent is extended or adjusted under 35 U.S.C. 154(b) by 270 days.

(21) Appl. No.: 16/075,122

(22) PCT Filed: Jan. 25, 2017

(86) PCT No.: PCT/US2017/014914
§ 371 (c)(1),
(2) Date: Aug. 2, 2018

(87) PCT Pub. No.: WO2017/136202
PCT Pub. Date: Aug. 10, 2017

(65) Prior Publication Data
US 2019/0038777 A1    Feb. 7, 2019

Related U.S. Application Data

(60) Provisional application No. 62/292,157, filed on Feb. 5, 2016.

(51) Int. Cl.
| A61K 48/00 | (2006.01) |
| A61K 9/00 | (2006.01) |
| A61K 45/06 | (2006.01) |
| A61P 25/00 | (2006.01) |
| A61P 37/00 | (2006.01) |
| C12N 15/86 | (2006.01) |

(52) U.S. Cl.
CPC ........ *A61K 48/0075* (2013.01); *A61K 9/0085* (2013.01); *A61K 45/06* (2013.01); *A61P 25/00* (2018.01); *A61P 37/00* (2018.01); *C12N 15/86* (2013.01); *C12N 2750/14143* (2013.01)

(58) Field of Classification Search
CPC .. A61K 48/0075; A61K 9/0085; C12N 15/86; C12N 2750/14143; A61P 25/00
See application file for complete search history.

(56) References Cited

U.S. PATENT DOCUMENTS

| 5,478,745 A | 12/1995 | Samulski |
| 6,110,743 A | 8/2000 | Levine et al. |
| 6,156,303 A | 12/2000 | Russell et al. |
| 8,692,332 B2 | 4/2014 | Chen et al. |
| 10,821,154 B2 * | 11/2020 | Passini ............... A61K 38/1709 |
| 2004/0063718 A1 * | 4/2004 | Michaelis ............ A61K 47/552 |
| | | 514/252.13 |
| 2009/0124591 A1 * | 5/2009 | Diamond ................ A61P 11/06 |
| | | 514/183 |
| 2011/0229971 A1 | 9/2011 | Knop et al. |
| 2012/0100606 A1 | 4/2012 | Zolotukhin |
| 2012/0135515 A1 | 5/2012 | Qu et al. |
| 2013/0072548 A1 | 3/2013 | Wright et al. |
| 2014/0037585 A1 | 2/2014 | Wright et al. |
| 2015/0252384 A1 * | 9/2015 | Kaspar ................... C07K 14/47 |
| | | 424/93.2 |
| 2016/0074474 A1 * | 3/2016 | Passini ................. A61K 9/0085 |
| | | 514/44 R |

FOREIGN PATENT DOCUMENTS

| EP | 3411484 B1 | 10/2023 |
| JP | 2015-521612 | 7/2015 |
| WO | WO 98/11244 A2 | 3/1998 |
| WO | WO 99/61601 A2 | 12/1999 |

(Continued)

OTHER PUBLICATIONS

Weight-for age Boys, Birth to 5 years, downloaded from https://www.who.int/childgrowth/standards/cht_wfa_boys_p_0_5.pdf?ua=1, on Nov. 7, 2020 (Year: 2020).*
Weight-for age Boys, 5 to 10 years, downloaded from https://www.who.int/growthref/cht_wfa_boys_perc_5_10years.pdf?ua=1, on Nov. 7, 2020 (Year: 2020).*
Weight-for age Girls, Birth to 5 years, downloaded from https://www.who.int/childgrowth/standards/cht_wfa_girls_p_0_5.pdf?ua=1, on Nov. 7, 2020 (Year: 2020).*
Weight-for age Girls, 5 to 10 years, downloaded from https://www.who.int/growthref/cht_wfa_girls_perc_5_10years.pdf?ua=1 on Nov. 7, 2020 (Year: 2020).*

(Continued)

*Primary Examiner* — Richard A Schnizer
(74) *Attorney, Agent, or Firm* — Klarquist Sparkman, LLP

(57) ABSTRACT

It is disclosed herein that ssAAV and scAAV vectors of the same serotype administered by injection into the cerebrospinal fluid (CSF) via the intracerebroventricular (ICV) or intrathecal (cisternal or lumbar) route exhibit different cellular tropisms in the central nervous system. Thus, a subject can be treated by injection into the CSF of ssAAV or scAAV vector encoding a therapeutic protein, such as an ssAAV9 or scAAV9 vector. The therapeutic protein can be targeted to specific cells using these vectors. In some embodiments, scAAV9 is utilized to achieve superior transduction in the hippocampus, cerebellum and cerebral cortex where both neurons, particularly Purkinje neurons, and glial cells (such as astrocytes) are transduced. In other embodiments, ssAAV9 is utilized to minimize transduction of astrocytes. In further embodiments, an immunosuppressive agent is also administered to the subject.

14 Claims, 6 Drawing Sheets

(56) References Cited

FOREIGN PATENT DOCUMENTS

| | | |
|---|---|---|
| WO | WO 00/28004 A1 | 5/2000 |
| WO | WO 00/28061 A2 | 5/2000 |
| WO | WO 2001/011034 A2 | 2/2001 |
| WO | WO 2001/092551 A2 | 12/2001 |
| WO | WO 2005/033321 A2 | 4/2005 |
| WO | WO 2009/013290 A1 | 1/2009 |
| WO | WO 2013/190059 A1 | 12/2013 |
| WO | WO 2014/178863 A1 | 11/2014 |
| WO | WO 2016/115503 A1 | 7/2016 |

OTHER PUBLICATIONS

Duque et al (Ann Neurol 2015;77:399-414) (Year: 2015).*
Glasscock et al (Biochemical and Biophysical Research Communications 417 (2012) 376-381) (Year: 2012).*
Robbins et al (Human Molecular Genetics, 23(17): 4559-4568, 2014) (Year: 2014).*
Armbruster et al., (Molecular Therapy—Methods & Clinical Development (2016) 3, 16060e, 8 pages) (Year: 2016).*
Wilson and Flotte (Hum Gene Ther, 31(3,4): 695-696, 2020) (Year: 2020).*
Hinderer et al., (Hum Gene Ther 2018;29:285-298) (Year: 2018).*
Federici et al., "Robust spinal motor neuron transduction following intrathecal delivery of AAV9 in pigs," *Gene Therapy* 19: 852-859 (Sep. 15, 2012).
Hironaka et al., "Enzyme replacement in the CSF to treat metachromatic leukodystrophy in mouse model using single intracerebroventricular injection of self-complementary AAV1 vector," *Scientific Reports* 5(1): 12 pages (Aug. 18, 2015).
Samaranch et al., "Strong cortical and spinal cord transduction after AAV7 and AAV9 delivery into the cerebrospinal fluid of nonhuman primates," *Human Gene Therapy* 24: 526-532 (e-PUB Mar. 20, 2013).
Donsante et al., "Intracerebroventricular delivery of self-complementary adeno-associated virus serotype 9 to the adult rat brain," Gene Therapy 23(5): 401-407 (ePub Jan. 29, 2016).
International Search Report from Parent PCT Application No. PCT/US2017/014914, 3 pages (mailed Apr. 10, 2017).
Meyer et al., "Improving single injection CSF delivery of AAV9-mediated gene therapy for SMA: A dose-response study in mice and nonhuman primates," *Molecular Therapy* 23(3): 477-487 (ePub Dec. 9, 2014).
SMN1 survival of motor neuron 1, telemetric [*Homo sapiens* (human)], Gene ID: 6606, *NCBI*, 16 pages (May 30, 2013).
Written Opinion from Parent PCT Application No. PCT/US2017/014914, 5 pages (mailed Apr. 10, 2017).
Altschul et al., "Basic local alignment search tool," *Journal of Molecular Biology* 215, No. 3 (1990): 403-410.
Altschul et al., "Gapped BLAST and PSI-BLAST: a new generation of protein database search programs," *Nucleic Acids Res.* 25, No. 17 (1997): 3389-3402.
Altschul et al., "Issues in searching molecular sequence databases," *Nature Genetics* 6: 119-129 (Feb. 1994).
Bach et al., "The defect in the Hunter syndrome: deficiency of sulfoiduronate sulfatase," *Proceedings of the National Academy of Sciences* 70, No. 7 (1973): 2134-2138.
Bastianelli, "Distribution of calcium-binding proteins in the cerebellum," *The Cerebellum* 2, No. 4 (2003): 242-262.
Benesova et al., "Quantification of astrocyte volume changes during ischemia in situ reveals two populations of astrocytes in the cortex of GFAP/EGFP mice," *Journal of Neuroscience Research* 87, No. 1 (2009): 96-111.
Beutler, "Enzyme replacement in Gaucher disease," *PLoS Med* 1, No. 2 (2004): 118-121.
Bitter, et al., "[33] Expression and secretion vectors for yeast," In *Methods in Enzymology*, vol. 153, pp. 516-544. Academic Press, 1987.

Brister and Muzyczka, "Mechanism of Rep-mediated adeno-associated virus origin nicking," *Journal of Virology* 74, No. 17 (2000): 7762-7771.
Brister and Muzyczka, "Rep-mediated nicking of the adeno-associated virus origin requires two biochemical activities, DNA helicase activity and transesterification," *Journal of Virology* 73, No. 11 (1999): 9325-9336.
Broekman et al., "Complete correction of enzymatic deficiency and neurochemistry in the GM1-gangliosidosis mouse brain by neonatal adeno-associated virus-mediated gene delivery," *Molecular Therapy* 15, No. 1 (2007): 30-37.
Burrow et al., "Enzyme reconstitution/replacement therapy for lysosomal storage diseases," *Current Opinion in Pediatrics* 19, No. 6 (2007): 628-635.
Chakrabarty et al., "Capsid serotype and timing of injection determines AAV transduction in the neonatal mice brain," *PloS One* 8, No. 6 (2013): e67680 (pp. 1-9).
Chao et al., "Several log increase in therapeutic transgene delivery by distinct adeno-associated viral serotype vectors," *Molecular Therapy* 2, No. 6 (2000): 619-623.
Charrow, "Enzyme replacement therapy for Gaucher disease," *Expert Opinion on Biological Therapy* 9, No. 1 (2009): 121-131.
Chiorini et al., "Cloning and characterization of adeno-associated virus type 5," *Journal of virology* 73, No. 2 (1999): 1309-1319.
Clarke, "The mucopolysaccharidoses: a success of molecular medicine," *Expert Rev. Mol. Med.*, vol. 10, el, pp. 1-18 (Jan. 2008).
Clarke, "Narrative review: Fabry disease," *Annals Internal Medicine* 20, No. 6 (2007): 425-433.
Connock et al., "The clinical effectiveness and cost-effectiveness of enzyme replacement therapy for Gaucher's disease: a systematic review," *Health Technology Assessment* (Winchester, England) 10, No. 24 (2006): iii-152.
Corpet, "Multiple sequence alignment with hierarchical clustering," *Nucleic Acids Research* 16, No. 22 (1988): 10881-10890.
Daya and Berns, "Gene therapy using adeno-associated virus vectors," *Clinical Microbiology Reviews* 21, No. 4: 583-593 (2008).
Dayton et al., "The advent of AAV9 expands applications for brain and spinal cord gene delivery," *Expert Opinion on Biological Therapy* 12, No. 6 (2012): 757-766.
Desnick et al., "Fabry disease, an under-recognized multisystemic disorder: expert recommendations for diagnosis, management, and enzyme replacement therapy," *Annals of Internal Medicine* 138, No. 4 (2003): 338-346.
Devereux et al., "A comprehensive set of sequence analysis programs for the VAX," *Nucleic Acids Research* 12, No. 1 (1984): 387-395.
Dirren et al., "Intracerebroventricular injection of adeno-associated virus 6 and 9 vectors for cell type-specific transgene expression in the spinal cord," *Human Gene Therapy* 25, No. 2 (2014): 109-120.
Do Carmo Costa et al., "Toward RNAi therapy for the polyglutamine disease Machado-Joseph disease," *Molecular Therapy* 21, No. 10 (2013): 1898-1908.
Dorfman and Lorincz, "Occurence of urinary acid mucopolysaccharides in the Hurler syndrome," *Proceedings of the National Academy of Sciences of the United States of America* 43, No. 6 (1957): 443-446.
Duque et al., "Intravenous administration of self-complementary AAV9 enables transgene delivery to adult motor neurons," *Molecular Therapy* 17, No. 7 (2009): 1187-1196.
Ellinwood et al., "Safe, efficient, and reproducible gene therapy of the brain in the dog models of Sanfilippo and Hurler syndromes," *Molecular Therapy* 19, No. 2 (2011): 251-259.
Feng and Doolittle, "Progressive sequence alignment as a prerequisite to correct phylogenetic trees," *Journal of Molecular Evolution* 25, No. 4 (1987): 351-360.
Fisher et al., "Transduction with recombinant adeno-associated virus for gene therapy is limited by leading-strand synthesis," *Journal of Virology* 70, No. 1 (1996): 520-532.
Fontana et al., "Astrocytes present myelin basic protein to encephalitogenic T-cell lines," *Nature* 307, No. 5948 (1984): 273-276.

(56) References Cited

OTHER PUBLICATIONS

Foust et al., "Intravascular AAV9 preferentially targets neonatal neurons and adult astrocytes," *Nature Biotechnology* 27, No. 1 (2009): 59-65.
Fu et al., "Correction of neurological disease of mucopolysaccharidosis IIIB in adult mice by rAAV9 trans-blood-brain barrier gene delivery," *Molecular Therapy* 19, No. 6 (2011): 1025-1033.
Fukuda et al., "Acid alpha-glucosidase deficiency (Pompe disease)," *Current Neurology and Neuroscience Reports* 7, No. 1 (2007): 71-77.
GENBANK® Accession No. AF 028704, retrieved from https://www.ncbi.nlm.nih.gov/nuccore/AF028704, dated Jan. 12, 1998 (3 pages).
GENBANK® Accession No. AF 028705, retrieved from https://www.ncbi.nlm.nih.gov/nuccore/AF028705, dated Jan. 12, 1998 (3 pages).
GENBANK® Accession No. AF 043303, retrieved from https://www.ncbi.nlm.nih.gov/nuccore/AF043303, dated May 20, 2010 (4 pages).
GENBANK® Accession No. AF 063497, retrieved from https://www.ncbi.nlm.nih.gov/nuccore/AF063497, dated Apr. 27, 1999 (3 pages).
GENBANK® Accession No. AF288061, retrieved from https://www.ncbi.nlm.nih.gov/nuccore/AF288061.1?report=genbank, dated Apr. 13, 2001 (1 page).
GENBANK® Accession No. AH009962, retrieved from https://www.ncbi.nlm.nih.gov/nuccore/AH009962, dated Aug. 25, 2016 (1 page).
GENBANK® Accession No. AY028223, retrieved from https://www.ncbi.nlm.nih.gov/nuccore/AY028223, dated Apr. 16, 2001 (1 page).
GENBANK® Accession No. AY028226, retrieved from https://www.ncbi.nlm.nih.gov/nuccore/AY028226, dated Apr. 16, 2001 (1 page).
GENBANK® Accession No. J 01901, retrieved from https://www.ncbi.nlm.nih.gov/nuccore/J01901, dated Apr. 27, 1993 (4 pages).
GENBANK® Accession No. J 02275, retrieved from https://www.ncbi.nlm.nih.gov/nuccore/J02275, dated May 22, 1995 (4 pages).
GENBANK® Accession No. NC 001358, retrieved from https://www.ncbi.nlm.nih.gov/nuccore/NC_001358.1?report=genbank, dated Feb. 10, 2015 (3 pages).
GENBANK® Accession No. NC 001401, retrieved from https://www.ncbi.nlm.nih.gov/nuccore/NC_001401, dated Aug. 13, 2018 (6 pages).
GENBANK® Accession No. NC 001510, retrieved from https://www.ncbi.nlm.nih.gov/nuccore/NC_001510, dated Aug. 13, 2018 (5 pages).
GENBANK® Accession No. NC 001540, retrieved from https://www.ncbi.nlm.nih.gov/nuccore/NC_001540, dated Aug. 13, 2018 (4 pages).
GENBANK® Accession No. NC 001701, retrieved from https://www.ncbi.nlm.nih.gov/nuccore/NC_001701, dated Aug. 13, 2018 (4 pages).
GENBANK® Accession No. NC 001729, retrieved from https://www.ncbi.nlm.nih.gov/nuccore/NC_001729, dated Aug. 13, 2018 (3 pages).
GENBANK® Accession No. NC 001829, retrieved from https://www.ncbi.nlm.nih.gov/nuccore/NC_001829, dated Aug. 13, 2018 (3 pages).
GENBANK® Accession No. NC 001862, retrieved from https://www.ncbi.nlm.nih.gov/nuccore/NC_001862.1?report=genbank, dated Jan. 12, 2004 (3 pages).
GENBANK® Accession No. NC 001863, retrieved from https://www.ncbi.nlm.nih.gov/nuccore/NC_001863.1?report=genbank, dated Jan. 12, 2004 (3 pages).
GENBANK® Accession No. NC 002077, retrieved from https://www.ncbi.nlm.nih.gov/nuccore/NC_002077, dated Aug. 13, 2018 (3 pages).
GENBANK® Accession No. U 89790, retrieved from https://www.ncbi.nlm.nih.gov/nuccore/U89790, dated Aug. 21, 1997 (3 pages).
GENBANK® Accession No. X01457, retrieved from https://www.ncbi.nlm.nih.gov/nuccore/X01457, dated Apr. 18, 2005 (3 pages).
Gholizadeh et al., "Transduction of the central nervous system after intracerebroventricular injection of adeno-associated viral vectors in neonatal and juvenile mice," *Human Gene Therapy Methods* 24, No. 4 (2013): 205-213.
Ghosh et al., "Long-term correction of murine glycogen storage disease type Ia by recombinant adeno-associated virus-1-mediated gene transfer," *Gene Therapy* 13, No. 4 (2006): 321-329.
Gray et al., "Global CNS gene delivery and evasion of anti-AAV-neutralizing antibodies by intrathecal AAV administration in non-human primates," *Gene Therapy* 20, No. 4 (2013): 450-459.
Gray et al., "Preclinical differences of intravascular AAV9 delivery to neurons and glia: A comparative study of adult mice and nonhuman primates," *Molecular Therapy* 19, No. 6 (2011): 1058-1069.
Haurigot et al., "Whole body correction of mucopolysaccharidosis IIIA by intracerebrospinal fluid gene therapy," *The Journal of Clinical Investigation* 123, No. 8 (2013): 3254-3271.
Henikoff and Henikoff, "Amino acid substitution matrices from protein blocks," *Proceedings of the National Academy of Sciences* 89, No. 22 (1992): 10915-10919.
Higgins and Sharp, "CLUSTAL: A package for performing multiple sequence alignment on a microcomputer," *Gene* 73, No. 1 (1988): 237-244.
Higgins and Sharp, "Fast and sensitive multiple sequence alignments on a microcomputer," *Bioinformatics* 5, No. 2 (1989): 151-153.
Hirata et al., "Design and packaging of adeno-associated virus gene targeting vectors," *Journal of Virology* 74, No. 10 (2000): 4612-4620.
Hitt and Graham, "Adenovirus vectors for human gene therapy," *Advances in Virus Research* 55: 479-505 (2000).
Hollak et al., "Treatment of lysosomal storage disorders: successes and challenges," *Journal of Inherited Metabolic Disease* 37, No. 4 (2014): 587-598.
La Salle et al., "An adenovirus vector for gene transfer into neurons and glia in the brain," *Science* 259, No. 5097 (1993): 988-990.
Lebkowski et al., "Adeno-associated virus: A vector system for efficient introduction and integration of DNA into a variety of mammalian cell types," *Molecular and Cellular Biology*, 8, No. 10 (1988): 3988-3996.
Levites et al., "Intracranial adeno-associated virus-mediated delivery of anti-pan amyloid β, amyloid β40, and amyloid β42 single-chain variable fragments attenuates plaque pathology in amyloid precursor protein mice," *Journal of Neuroscience* 26, No. 46 (2006): 11923-11928.
McCarty et al., "Adeno-associated virus terminal repeat (TR) mutant generates self-complementary vectors to overcome the rate-limiting step to transduction in vivo," *Gene Therapy* 10, No. 26 (2003): 2112-2118.
McCarty et al., "Self-complementary recombinant adeno-associated virus (scAAV) vectors promote efficient transduction independently of DNA synthesis," *Gene Therapy* 8, No. 16 (2001): 1248-1254.
McCarty, "Self-complementary AAV vectors; advances and applications," *Molecular Therapy* 16, No. 10 (2008): 1648-1656.
McLean et al., "Widespread neuron-specific transgene expression in brain and spinal cord following synapsin promoter-driven AAV9 neonatal intracerebroventricular injection," *Neuroscience Letters* 576 (2014): 73-78 (available on-line May 29, 2014).
Mingozzi and High, "Immune responses to AAV vectors: overcoming barriers to successful gene therapy," *Blood* 122, No. 1 (2013): 23-36.
Muenzer et al. "A phase II/III clinical study of enzyme replacement therapy with idursulfase in mucopolysaccharidosis II (Hunter syndrome)," *Genetics in Medicine* 8, No. 8 (Aug. 2006): 465-473.
Muramatsu et al., "Nucleotide sequencing and generation of an infectious clone of adeno-associated virus 3," *Virology* 221, No. 1 (1996): 208-217.
Nathwani et al., "Adenovirus-associated virus vector-mediated gene transfer in hemophilia B," *New England Journal of Medicine* 365, No. 25 (2011): 2357-2365.

(56) References Cited

OTHER PUBLICATIONS

Nathwani et al., "Self-complementary adeno-associated virus vectors containing a novel liver-specific human factor IX expression cassette enable highly efficient transduction of murine and nonhuman primate liver," *Blood* 107, No. 7 (2006): 2653-2661.

Needleman and Wunsch, "A general method applicable to the search for similarities in the amino acid sequence of two proteins," *Journal of Molecular Biology* 48 (1970): 443-453.

Oberheim et al., "Uniquely hominid features of adult human astrocytes," *Journal of Neuroscience* 29, No. 10 (2009): 3276-3287.

Passini et al., "Translational fidelity of intrathecal delivery of self-complementary AAV9-survival motor neuron 1 for spinal muscular atrophy," *Human Gene Therapy* 25, No. 7 (Jul. 2014): 619-630 (published on-line Mar. 10, 2014).

Pearson and Lipman, "Improved tools for biological sequence comparison," *Proceedings of the National Academy of Science USA* 85 (1988): 2444-2448.

Raben et al., "Replacing acid α-glucosidase in Pompe disease: recombinant and transgenic enzymes are equipotent, but neither completely clears glycogen from type II muscle fiber," *Molecular Therapy* 11, No. 1 (2005): 48-56 (published on-line Nov. 2, 2004).

Raben et al., "Role of autophagy in the pathogenesis of Pompe disease," *Acta Myologica* 26, No. 1 (2007): 45-48.

Rohrbach and Clarke, "Treatment of lysosomal storage disorders, Progress with enzyme replacement therapy," *Drugs* 67, No. 18 (2007): 2697-2716.

Samaranch et al., "AAV9-mediated expression of a non-self protein in nonhuman primate central nervous system triggers widespread neuroinflammation driven by antigen-presenting cell transduction," *Molecular Therapy* 22, No. 2 (2014): 329-337.

Samaranch et al., "Adeno-associated virus serotype 9 transduction in the central nervous system of nonhuman primates," *Human Gene Therapy* 23, No. 4 (2012): 382-389.

Samulski et al., "A recombinant plasmid from which an infectious adeno-associated virus genome can be excised in vitro and its use to study viral replication," *Journal of Virology* 61, No. 10 (1987): 3096-3101.

Samulski et al., "Helper-free stocks of recombinant adeno-associated viruses: normal integration does not require viral gene expression," *Journal of Virology* 63, No. 9 (Sep. 1989): 3822-3828.

Samulski et al., "Rescue of adeno-associated virus from recombinant plasmids: gene correction within the terminal repeats of AAV," *Cell* 33, No. 1 (1983): 135-143.

Sands and Davidson, "Gene therapy for lysosomal storage diseases," *Molecular Therapy* 13, No. 5 (May 2006):839-49.

Settembre et al., "A block of autophagy in lysosomal storage disorders," *Human Molecular Genetetics* 17, No. 1 (2008): 119-129.

Smith and Waterman, "Comparison of biosequences," *Advances in Applied Mathematics* 2, No. 4 (1981): 482-489.

Snyder et al., "Features of the adeno-associated virus origin involved in substrate recognition by the viral Rep protein," *Journal of Virology* 67, No. 10 (1993): 6096-6104.

Snyder et al., "In vitro resolution of covalently joined AAV chromosome ends," *Cell* 60, No. 1 (1990): 105-113.

Sofroniew et al., "Astrocytes: biology and pathology," *Acta Neuropathologica* 119, No. 1 (2010): 7-35.

SPINRAZA® Prescribing Information, retrieved from https://www.accessdata.fda.gov/spl/data/f35693e6-6a5f-42e0-a5ab-bd49724ca03e/f35693e6-6a5f-42e0-a5ab-bd49724ca03e.XML, revised Dec. 2016, 13 pages.

Stratford-Perricaudet et al., "Widespread long-term gene transfer to mouse skeletal muscles and heart," *J. Clin. Invest.* 90, No. 2 (1992): 626-630.

Tolar and Orchard, "α-L-iduronidase therapy for mucopolysaccharidosis type I," *Biologics: Targets & Therapy* 2, No. 4 (2008): 743-751.

Tomatsu et al., "Enzyme replacement therapy in a murine model of Morquio A syndrome," *Human Molecular Genetics* 17, No. 6 (2008): 815-824.

Van der Beek et al., "Pompe disease (glycogen storage disease type II): clinical features and enzyme replacement therapy," *Acta Neurologica Belgica* 106, No. 2 (2006): 82-86.

Wang et al., "Rapid and highly efficient transduction by double-stranded adeno-associated virus vectors in vitro and in vivo," *Gene Therapy* 10, No. 26 (2003): 2105-2111.

Xia et al., "RNAi suppresses polyglutamine-induced neurodegeneration in a model of spinocerebellar ataxia," *Nature Medicine* 10, No. 8 (Aug. 2004): 816-820.

Xiao et al., "Gene therapy vectors based on adeno-associated virus type 1," *Journal of Virology* 73, No. 5 (May 1999): 3994-4003.

Zarate and Hopkin, "Fabry's disease," *The Lancet* 372, No. 9647 (2008): 1427-1435.

ZOLGENSMA® Prescribing Information, retrieved from https://www.accessdata.fda.gov/spl/data/68cd4f06-70e1-40d8-bedb-609ec0afa471/68cd4f06-70e1-40d8-bedb-609ec0afa471.XML, last updated May 2019, 14 pages.

Ozawa "Gene therapy using AAV vectors," *Drug Delivery System* 22: 643-650 (Jun. 22, 2007) (w/English language Abstract).

Andersson and Alestig, "The penetration of doxycycline into CSF," *Scand. J. Infect. Dis, Supp.* 9: 17-19 (1976).

Ben-Zvi et al., "Mfsd2a is critical for the formation and function of the blood-brain barrier," *Nature* 509: 507, 18 pages (May 22, 2014).

Doxycycline Overview by Louisiana Department of Health and Hospitals (https://ldh.la.gov/assets/oph/Center-PHCH/Center-CH/infectious-epi/VetInfo/VetAntibioResSen/LADDL/AntimicrobialClasses/tetracyclines/Doxycycline.pdf).

Foust et al., "Rescue of the spinal muscular atrophy phenotype in a mouse model by early postnatal delivery of SMN," *Nat. Biotechnol.* 28(3): 271-274 (Mar. 2010).

Le et al., "Temporal requirement for high SMN expression in SMA mice," *Human Molecular Genetics* 20(18): 3578-3591 (e-Pub Jun. 13, 2011).

Moretti et al., "Blood-brain barrier dysfunction in disorders of the developing brain," *Frontiers in Neuroscience* 9(40): 15 pages (Feb. 17, 2015).

Saunders et al., "The neonatal blood-brain barrier is functionally effective, and immaturity does not explain differential targeting of AAV9," *Nature Biotechnology* 27(9): 804 (Sep. 2009).

Slikker, "The developing nervous system," *Comprehensive Biotechnology*, Elsevier, Ltd., Third Edition, U.S.A., vol. 11, pp. 227-288 (2011).

Strauss et al., "Onasemnogene abeparvovec for presymptomatic infants with two copies of SMN2 at risk for spinal muscular atrophy type 1: the Phase III SPRINT trial," *Nature Medicine* 28: 1381-1389 (Jul. 2022).

Finkel et a., "Intrathecal onasemnogene abeparvovec for sitting, nonambulatory patients with spinal muscular atrophy: phase I ascending-dose study (STRONG)," *Journal of Neuromuscular Diseases* 10: 389-404 (epub Mar. 9, 2023).

Norvartis, "Q12023 Results Investor Presentation," available on-line at: https://protect-us.mimecast.com/s/X0BJC680LnSrv7gPFmaud2?domain=novartis.com, 94 pages (downloaded on Jun. 2, 2023).

Clinical Trial No. NCT05386680, "Phase IIIb, open-label, multi-center study to evaluate safety, tolerability and efficacy of OAV101 administered intrathecally to participants with SMA who discontinued treatment with nusinersen or risdiplam (STRENGTH)," available on line at: https://clinicaltrials.gov/ct2/show/NCT05386680?term=NCT05386680&draw=2&rank=1 (May 23, 2022).

Clinical Trial No. NCT05089656, "Efficacy and safety of intrathecal OAV101 (AVXS-101) in pediatric patients with type 2 spinal muscular atrophy (SMA) (STEER)," available on-line at: https://clinicaltrials.gov/ct2/show/NCT05089656?term=NCT05089656&draw=1&rank=1 (Oct. 22, 2021).

Efficacy and Safety of Intrathecal OAV101 (AVXS-101) in Pediatric Patients With Type 2 Spinal Muscular Atrophy (SMA) (STEER), (Last updated posted Nov. 6, 2023) retrieved from: https://clinicaltrials.gov/study/NCT05089656 (12 pages).

European Medicines Agency, Assessment report, Zolgensma, (Mar. 26, 2020), retrieved from: zolgensma-epar-public-assessment-report_en.pdf (europa.eu) (150 pages).

(56) References Cited

OTHER PUBLICATIONS

Rene and Parks, "Expanding the availability of onasemnogene abeparvovec to older patients: The evolving treatment landscape for spinal muscular atrophy," Pharmaceutics 15 (Jun. 19, 2023): 1764, 12 pages.

Study of Intrathecal Administration of Onasemnogene Abeparvovec-xioi for Spinal Muscular Atrophy (STRONG) (Last updated Apr. 24, 2023), retrieved from Results Posted | Study of Intrathecal Administration of Onasemnogene Abeparvovec-xioi for Spinal Muscular Atrophy | ClinicalTrials.gov.

Results Published from STRONG Trial of Zolgensma (Apr. 12, 2023) retrieved from: https://smauk.org.uk/information/results-published-from-strong-trial-of-zolgensma/, (3 pages).

Naveed and Calderon, "Onasemnogene Abeparvovec (AVXS-101) for the Treatment of Spinal Muscular Atrophy," J Pediatr Pharmacol Ther. 26(5): 437-444 (2021).

\* cited by examiner

FIG. 1A
FIG. 1B
FIG. 1C
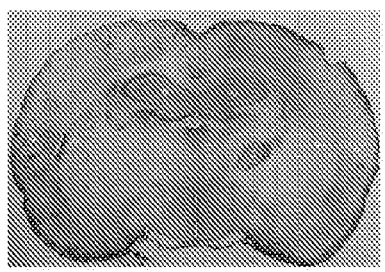
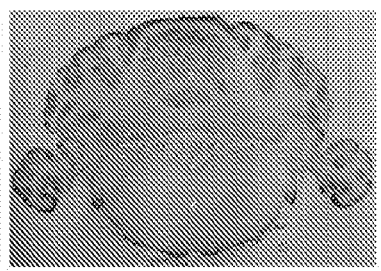
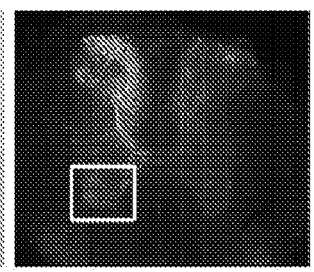
FIG. 1D
FIG. 1E
FIG. 1F
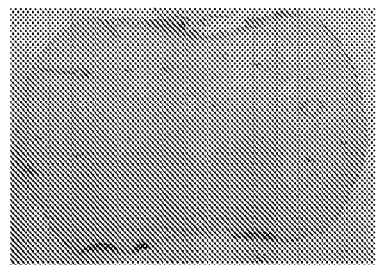
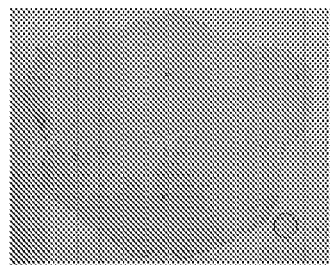
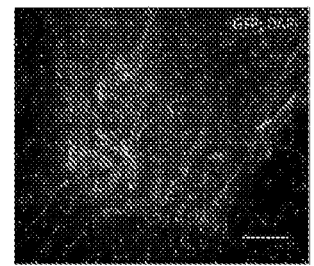

INJECTION OF SINGLE-STRANDED OR SELF-COMPLEMENTARY ADENO-ASSOCIATED VIRUS 9 INTO THE CEREBROSPINAL FLUID

CROSS REFERENCE TO RELATED APPLICATION

This is a § 371 U.S. national stage of International Application No. PCT/US2017/014914, filed Jan. 25, 2017, which was published in English under PCT Article 21(2), which claims the benefit of U.S. Provisional Application No. 62/292,157, filed Feb. 5, 2016, which is incorporated by reference herein.

FIELD

Compositions and methods are described for targeting treatment to the central nervous system (CNS); specifically dosing regimens that utilize adeno-associated virus (AAV), specifically AAV9, administered by injection into the cerebrospinal fluid (CSF) via the intracerebroventricular (ICV) or intrathecal (cisternal or lumbar) route in order to target treatment to different cells in the CNS.

PARTIES TO JOINT RESEARCH AGREEMENT

Emory University and Regenxbio are parties to a joint research agreement.

BACKGROUND

Gene therapy has long been studied in animal models to treat diseases of the central nervous system (CNS). A wide variety of inherited metabolic diseases, such as lysosomal storage diseases, impact the brain, causing mental retardation and neurodegeneration. CNS disorders substantially impact the quality of life of patients and their family members, leading to loss of independence and difficulties in communication. Direct delivery of therapeutic genes to the brain offers a potential treatment for these diseases that could circumvent problems found with systemic therapies. For example, neutralizing antibodies in the CNS are less of a concern, (Gray et al., 2013, Gene Therapy 20: 450-459) and the risk of an immune response to the vector and/or the transgene seems to be lower, (Mingozzi and High, Blood. 2013 Jul. 4; 122(1):23-36) although this risk is still not zero (Ellinwood et al., Mol Ther. 2011 February; 19(2):251-9).

For treating disorders that affect cells throughout the CNS, such as lysosomal storage diseases, one challenge for gene therapy is to achieve adequate transduction throughout the brain and spinal cord. One vector, adeno-associated virus serotype 9 (AAV9) has the ability to transduce cells of the CNS, and displays the ability to bypass the blood brain barrier (BBB). After intravenous injection of high doses of AAV9 vector, studies have shown transduction of the CNS in rodents and nonhuman primates (NHPs). (E.g., see, Foust, et al., 2009, Nat. Biotechnol. 27: 59-65; Duque et al., 2009, Mol. Ther. 17: 1187-1196; Fu et al., 2011, Mol. Ther. 19: 1025-1033; and Gray et al., 2011, Mol. Ther. 19:1058-1069). Distribution of AAV9 to the spinal cord after intrathecal administration to newborn mice, pigs and monkeys was also investigated. (Passini et al., 2014, Human Gene Therapy 25: 619-630). A recent study compared vascular delivery to CSF delivery of AAV9 in NHPs. Both delivery routes were reported to generate similar distribution patterns and tropism—greater astrocytic than neuronal tropism. Although CSF administration generated a greater magnitude of CNS transduction, it did not shield against AAV antibodies. (Samaranch et al., 2012, Hum Gene Ther 23: 382-389). Considerable innovation is expected to be required to tackle the significant issues raised in these and other studies.

SUMMARY

Compositions and methods are described for treating a human subject by administering a therapeutically effective amount of a single stranded adeno-associated virus (ssAAV) or self-complementary adeno-associated virus (scAAV) vector, such as an ssAAV9 or scAAV9 vector, encoding a therapeutic gene product (e.g., a therapeutic protein or other therapeutic agent), by injecting the ssAAV or scAAV vector into the cerebrospinal fluid (CSF) via the intracerebroventricular (ICV) or intrathecal (cisternal or lumbar) route of administration. When the ICV route is utilized, bilateral ICV injection may be preferable in a clinical setting.

The invention is based, in part, on the inventors' discovery that ssAAV and scAAV vectors of the same serotype, such as AAV9, when delivered to the CSF exhibit different cellular tropisms in the CNS. This is surprising, since to our best knowledge, there are no previous reports of ssAAV and scAAV vectors of the same serotype exhibiting different cellular tropisms.

In some embodiments, scAAV9 is administered to the CSF to achieve superior transduction in the hippocampus, cerebellum and cerebral cortex where both neurons and glial cells (such as astrocytes) are transduced and there is substantial transduction of cells in the cerebellum, particularly of Purkinje neurons. This approach may be particularly desirable where the transgene product is not secreted and, therefore, will not result in cross correction of untransformed cells. However, in diseases where astrocytosis and/or encephalitis are of concern, in specific non-limiting examples, an immunosuppressive agent is also administered.

For example, one embodiment involves delivering a non-secreted therapeutic protein to the CNS in a human subject in need thereof, comprising administering to the subject an effective amount of a scAAV9 encoding the non-secreted therapeutic protein, wherein the scAAV9 is administered by injection into the CSF via an intracerebroventricular, intrathecal cisternal, or intrathecal lumbar route. Particular embodiments result in delivery of the therapeutic protein to neurons and glial cells of the brain. This method can further comprise administering a therapeutically effective amount of an immunosuppressive agent as a co-therapy. In certain embodiments, the therapeutic protein is not SMN1.

Another exemplary embodiment involves delivering a therapeutic protein to neurons, Purkinje neurons and/or astrocytes in a human subject in need thereof, comprising administering to the subject an effective amount of a scAAV9 encoding the therapeutic protein, wherein the scAAV9 is administered by injection into the CSF via an intracerebroventricular, intrathecal cisternal, or intrathecal lumbar route. This method can further comprise administering a therapeutically effective amount of an immunosuppressive agent as a co-therapy.

In other embodiments, ssAAV9 is administered to the CSF to minimize transduction of astrocytes. In specific non-limiting examples, ssAAV9 can be used to express secreted transgene products where cross-correction can result in effective treatment of untransformed CNS cells. In specific non-limiting examples, an immunosuppressive agent is also administered.

Formulations of ssAAV and scAAV suitable for ICV delivery to human subjects and therapeutically effective doses of ssAAV9 and scAAV9 are disclosed.

The foregoing and other objects, features, and advantages of the invention will become more apparent from the following detailed description, which proceeds with reference to the accompanying figures.

BRIEF DESCRIPTION OF THE DRAWINGS

FIGS. 1a-1f. Widespread transduction of the CNS occurs following ICV scAAV9 delivery. Sprague-Dawley rats were sacrificed three weeks after receiving ICV injection of scAAV9-GFP or saline. (a, b, d, e) Brain and spinal cord sections were stained for GFP (black stain). Sections from a high-dose rats are shown at approximately (a) 2.1 mm and (b) 11.3 mm caudal of bregma. Comparable regions from a saline-treated rats are shown, revealing limited background staining (d,e). Notably, there was substantial transduction of the (a) cerebral cortex, hippocampus, and (b) cerebellum. Transduction was also high on the right side of the brain in the proximity of the injection tract. Deeper brain structures showed less transduction. (c) Transduction of the spinal cord was evaluated by immunofluorescence (green stain). A ventral horn, boxed in (c), is shown magnified in (f). In contrast to the brain, there was little staining of cell bodies in the gray matter. Instead, the majority of the GFP staining appeared to be axons. Abbreviations: BS, brain stem; Cb, cerebellum; Cpu, caudate putamen; Cx, cerebral cortex; Hp, hippocampus; T, thalamus. The scale bar in (f) represents 100 um.

DETAILED DESCRIPTION

Figure 2A:
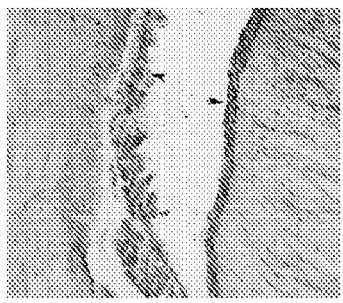
FIGS. 2a-2g. scAAV9 transduces several cell types when delivered by ICV injection in the rat. (a) Brain sections from scAAV9-GFP-treated rats stained for GFP (black), demonstrate significant transduction of the choroid plexus (arrowhead) and ependyma (arrow), particularly in the injected ventricle. (b-g) Brain sections were costained for GFP (green) and cell markers (red): (b) NeuN, (c) Fox2, (d) calbindin, (e) GFAP, (f) GAD67, and (g) S100β. Colocalization of between GFP and cell markers is indicated by arrows. (b) A representative image from a high-dose animal shows colocalization of NeuN and GFP in hippocampal neurons. Colocalization with NeuN was also observed in the cerebral cortex. (c) The cerebellum of a low-dose animal is shown. Purkinje cells, identified by their elaborate dendritic tree and the presence of Fox2 in the nucleus, are the primary cell transduced. (d) Staining for calbindin, which stains a variety of neurons including Purkinje cells, also showed extensive colocatization with GFP (orange to yellow), supporting the conclusion that the majority of GFP expression in the cerebellum is due to Purkinje cell transduction. GFP$^+$ cells with morphology reminiscent of astrocytes were observed regularly in the cerebral cortex. Staining for (d) GFAP, a marker for astrocytes, and (e) GAD67, a marker for interneurons, failed to show colocalization with GFP for these cells. (f) However, S100β, a marker for a subset of astrocytes, stained most, if not all, of the cells with this morphology.

Various routes of administration (intrathecal, intracisternal, or intraventricular) have been investigated in animal models for the delivery of viral vectors to the cerebrospinal fluid (CSF) with the goal of achieving transduction throughout the brain and spinal cord (CNS) for the potential treatment of disorders that affect the CNS by gene therapy. One vector in particular, adeno-associated virus serotype 9 (AAV9), has the ability to transduce many regions of the CNS following CSF delivery (Dayton et al., Expert Opin Biol Ther. 2012 June; 12(6):757-66). In this regard, intracerebroventricular (ICV) delivery of AAV9 has been studied in neonatal or juvenile mouse models for delivering genes to the CNS via the cerebrospinal fluid (CSF) (McClean et al., 2014, Neurosci. Lett. 576:73-8; Levites et al., J. Neurosci. 26:11923-8; Gholizadeh et al., 2013, 24:205-13; Dirren et al., 2014, Hum. Gene Ther. 25:109-20. However, the brain is not fully developed in these animal models, and remarkable differences in transduction patterns were noted when treatment age varied. (Chakrabarty, et al. 2013, PLoS One 8:e67680). It is not clear how AAV9 will perform in the adult brain, and most importantly, in human subjects. With the exception of one canine study (Haurigot et al. 2013, J. Clin. Invest. July 1), little is known about the biodistribution of AAV9 following ICV injection into animals larger than mice.

Indeed, Chakrabarty et al. (2013) have shown remarkable differences in transduction patterns when the treatment age was varied.(9) In addition the small size and resilience of the neonatal mouse allows for the delivery of large doses that may not be practical in a clinical setting. For instance, one mouse study administered a dose of ~$3\times10^{14}$ vector genomes (vg) per kilogram.(10) This dose is more than 100 times greater than that used in a recent clinical trial for hemophilia that was administered intravenously.(11)

Prior to the present disclosure, little was known (12) about the biodistribution of AAV9 following ICV injection into animals larger than mice. In addition, distribution of ICV self-complimentary AAV9 (scAAV9), which is expected to yield better transduction than the traditional single-stranded AAV9 (ssAAV9), was not examined outside of the neonatal mouse. The dose-response relationship for ICV-delivered scAAV9 in the adult rat was examined using doses in the range that could be used clinically in a human trial. This study served as the foundation for a comparative study in a large animal model, the farm pig. The studies disclosed herein provide dosing decisions for humans, such as using ICV administration of ssAAV9 or scAAV9. The studies disclosed herein also document that ssAAV and scAAV vectors of the same serotype (delivered ICV) exhibit different cellular tropisms in the CNS. This result could not have been predicted, and forms the basis for the improved methods and compositions described herein for delivering therapeutic proteins to the CNS.

Specifically, superior transduction in the hippocampus, cerebellum and cerebral cortex of both neuronal and glial cells including astrocytes is achieved by scAAV9. To treat conditions where it is desirable to transduce all cells (including glial cells such as astrocytes) to treat disease (e.g., where the transgene product is not secreted and cross-correction does not occur or is not reliable) scAAV9 can be used. However, in certain diseases/conditions, where there is a concomitant concern re resulting astrocytosis/encephalitis, in some embodiments, an immunosuppressive agent also can be administered. Thus, in some examples, concurrent immunosuppression therapy can be used to minimize the risk of side effects.

In additional embodiments, in order to treat a disease wherein central nervous system (CNS) inflammation/encephalitis is a concern, ssAAV9 can be used to minimize transduction of astrocytes and induction of astrocytosis/encephalitis. In further embodiments, an immunosuppressive agent also can be administered. In yet other embodiments, ssAAV9 treatment can be used for secreted transgene products where cross-correction can result in effective treatment of untransformed CNS cells.

Dosages of ssAAV9, and scAAV9 and formulations that could be used for injection into the CSF in human subjects follow:
 About $4.4 \times 10^{13}$ to about $1.33 \times 10^{14}$ GC total dose (flat dose) for infants
 About $1.56 \times 10^{14}$ to about $4.67 \times 10^{14}$ GC total dose (flat dose) for adults
 About $7.4 \times 10^{12}$ to about $1.86 \times 10^{14}$ GC total dose (flat dose) for infants
 About $2.59 \times 10^{13}$ to about $6.51 \times 10^{14}$ GC total dose (flat dose) for adults Thus, the dose can be:
 $4.4 \times 10^{-}$ to $1.33 \times 10^{14}$ GC total dose (flat dose) for infants
 $1.56 \times 10^{14}$ to $4.67 \times 10^{14}$ GC total dose (flat dose) for adults
 $7.4 \times 10^{12}$ to $1.86 \times 10^{14}$ GC total dose (flat dose) for infants
 $2.59 \times 10^{13}$ to $6.51 \times 10^{14}$ GC total dose (flat dose) for adults Other doses of use are:
 3-9 months: About $6.0 \times 10^{13}$ to about $1.9 \times 10^{14}$ GC; or about $1.1 \times 10^{14}$ to about $2.79 \times 10^{14}$ GC total dose (flat dose);
 9-36 months: About $1.0 \times 10^{14}$ to about $3.3 \times 10^{14}$ GC; or about $1.85 \times 10^{13}$ to about $4.65 \times 10^{14}$ GC total dose (flat dose);
 3-12 years: About $1.2 \times 10^{14}$ to about $3.96 \times 10^{14}$ GC; or about $2.2 \times 10^{13}$ to about $5.58 \times 10^{14}$ GC total dose (flat dose);
 12+ years: About $1.4 \times 10^{14}$ to about $4.62 \times 10^{14}$ GC; or about $2.59 \times 10^{13}$ GC to about $6.51 \times 10^{14}$ GC total dose (flat dose).

Thus, other doses of use are:
 3-9 months: $6.0 \times 10^{13}$ to $1.9 \times 10^{14}$ GC; or $1.1 \times 10^{14}$ to $2.79 \times 10^{14}$ GC total dose (flat dose);
 9-36 months: $1.0 \times 10^{14}$ to $3.3 \times 10^{14}$ GC; or $1.85 \times 10^{13}$ to $4.65 \times 10^{14}$ GC total dose (flat dose);
 3-12 years: $1.2 \times 10^{14}$ to $3.96 \times 10^{14}$ GC; or $2.2 \times 10^{13}$ to $5.58 \times 10^{14}$ GC total dose (flat dose);
 12+ years: $1.4 \times 10^{14}$ to $4.62 \times 10^{14}$ GC; or $2.59 \times 10^{13}$ GC to $6.51 \times 10^{14}$ GC total dose (flat dose).

In another embodiment, the dose for a newborn is
 About $4.4 \times 10^{13}$ to about $1.32 \times 10^{14}$ (flat dose); or
 About $7.4 \times 10^{12}$ to about $1.86 \times 10^{14}$ GC total (flat dose).

Thus, the dose for a newborn can be:
 $4.4 \times 10^{13}$ to $1.32 \times 10^{14}$ (flat dose); or
 $7.4 \times 10^{12}$ to $1.86 \times 10^{14}$ GC total (flat dose).

In further embodiments, the dose is increased two-fold, thus the dose can be:
 About $8.8 \times 10^{13}$ to about $2.66 \times 10^{14}$ GC total dose (flat dose) for infants
 About $3.21 \times 10^{14}$ to about $9.34 \times 10^{14}$ GC total dose (flat dose) for adults
 About $14.8 \times 10^{12}$ to about $3.72 \times 10^{14}$ GC total dose (flat dose) for infants
 About $5.18 \times 10^{13}$ to about $13.02 \times 10^{14}$ GC total dose (flat dose) for adults Thus, the dose can be:
 $8.8 \times 10^{13}$ to $2.66 \times 10^{14}$ GC total dose (flat dose) for infants
 $3.21 \times 10^{14}$ to $9.34 \times 10^{14}$ GC total dose (flat dose) for adults
 $14.8 \times 10^{12}$ to $3.72 \times 10^{14}$ GC total dose (flat dose) for infants
 $5.18 \times 10^{13}$ to $13.02 \times 10^{14}$ GC total dose (flat dose) for adults Other doses of use are:
 3-9 months: About $1.20 \times 10^{14}$ to about $3.8 \times 10^{14}$ GC; or about $2.2 \times 10^{14}$ to about $5.58 \times 10^{14}$ GC total dose (flat dose);
 9-36 months: About $2.0 \times 10^{14}$ to about $6.6 \times 10^{14}$ GC; or about $3.7 \times 10^{13}$ to about $9.3 \times 10^{14}$ GC total dose (flat dose);
 3-12 years: About $2.4 \times 10^{14}$ to about $7.92 \times 10^{14}$ GC; or about $4.4 \times 10^{13}$ to about $1.116 \times 10^{15}$ GC total dose (flat dose);
 12+ years: About $2.8 \times 10^{14}$ to about $9.24 \times 10^{14}$ GC; or about $5.18 \times 10^{13}$ GC to about $1.302 \times 10^{15}$ GC total dose (flat dose).

Thus, other doses of use are:
 3-9 months: $1.20 \times 10^{14}$ to $3.8 \times 10^{14}$ GC; or $2.2 \times 10^{14}$ to $5.58 \times 10^{14}$ GC total dose (flat dose);
 9-36 months: $2.0 \times 10^{14}$ to $6.6 \times 10^{14}$ GC; or $3.7 \times 10^{13}$ to about $9.3 \times 10^{14}$ GC total dose (flat dose);
 3-12 years: $2.4 \times 10^{14}$ to $7.92 \times 10^{14}$ GC; or $4.4 \times 10^{13}$ to $1.116 \times 10^{15}$ GC total dose (flat dose);
 12+ years: $2.8 \times 10^{14}$ to $9.24 \times 10^{14}$ GC; or $5.18 \times 10^{13}$ GC to $1.302 \times 10^{15}$ GC total dose (flat dose).

In another embodiment, the dose for a newborn is
 About $8.8 \times 10^{13}$ to about $2.64 \times 10^{14}$ (flat dose); or
 About $1.48 \times 10^{13}$ to about $3.72 \times 10^{14}$ GC total (flat dose).

Thus, the dose for a newborn can be:
 $8.8 \times 10^{13}$ to $2.64 \times 10^{14}$ (flat dose); or
 $1.48 \times 10^{13}$ to $3.72 \times 10^{14}$ GC total (flat dose).

In other embodiments, the dose is decreased, and ½ the original dose is utilized. Thus, the dose can be:
 About $2.2 \times 10^{13}$ to about $6.65 \times 10^{13}$ GC total dose (flat dose) for infants
 About $7.8 \times 10^{13}$ to about $2.335 \times 10^{14}$ GC total dose (flat dose) for adults
 About $3.7 \times 10^{12}$ to about $9.3 \times 10^{13}$ GC total dose (flat dose) for infants
 About $1.295 \times 10^{13}$ to about $3.225 \times 10^{14}$ GC total dose (flat dose) for adults Thus, the dose can be:
 $2.2 \times 10^{13}$ to $6.65 \times 10^{13}$ GC total dose (flat dose) for infants
 $7.8 \times 10^{13}$ to $2.335 \times 10^{14}$ GC total dose (flat dose) for adults
 $3.7 \times 10^{12}$ to $9.3 \times 10^{13}$ GC total dose (flat dose) for infants 1.295×10$^{13}$ to 3.225×10$^{14}$ GC total dose (flat dose) for adults Other doses of use are:
- 3-9 months: About 3.0×10$^{13}$ to about 9.5×10$^{13}$ GC; or about 5.5×10$^{13}$ to about 1.395×10$^{14}$ GC total dose (flat dose);
- 9-36 months: About 5×10$^{13}$ to about 1.65×10$^{14}$ GC; or about 9.25×10$^{12}$ to about 2.325×10$^{14}$ GC total dose (flat dose);
- 3-12 years: About 6×10$^{13}$ to about 1.98×10$^{14}$ GC; or about 1.1×10$^{13}$ to about 2.79×10$^{14}$ GC total dose (flat dose);
- 12+ years: About 7×10$^{13}$ to about 2.31×10$^{14}$ GC; or about 1.295×10$^{13}$ GC to about 3.225×10$^{14}$ GC total dose (flat dose).

Thus, other doses of use are:
- 3-9 months: 3.0×10$^{13}$ to 9.5×10$^{13}$ GC; or 5.5×10$^{13}$ to 1.395×10$^{14}$ GC total dose (flat dose);
- 9-36 months: 5×10$^{13}$ to 1.65×10$^{14}$ GC; or 9.25×10$^{12}$ to 2.325×10$^{14}$ GC total dose (flat dose);
- 3-12 years: 6×10$^{13}$ to 1.98×10$^{14}$ GC; or 1.1×10$^{13}$ to 2.79×10$^{14}$ GC total dose (flat dose);
- 12+ years: 7×10$^{13}$ to 2.31×10$^{14}$ GC; or 1.295×10$^{13}$ GC to 3.225×10$^{14}$ GC total dose (flat dose).

In another embodiment, the dose for a newborn is
About 2.2×10$^{13}$ to about 6.6×10$^{13}$ (flat dose); or
About 3.7×10$^{12}$ to about 9.3×10$^{13}$ GC total (flat dose).

Thus, the dose for a newborn can be:
2.2×10$^{13}$ to 6.6×10$^{13}$ (flat dose); or
3.7×10$^{12}$ to 9.3×10$^{13}$ GC total (flat dose).

In the context of dose, as shown above, "about" is within 5%. Note that genome content, "GC," is equivalent to viral genomes, "vg." One of skill in the art can readily determine GC. For example, GC can be determined by quantitative polymerase chain reaction (qPCR) using methods known in the art.

Terms

Adeno-associated Virus (AAV): AAV is a small virus that infects humans and some other primate species. AAV is not currently known to cause disease and the virus causes a very mild immune response. AAV can infect both dividing and non-dividing cells and may incorporate its genome into that of the host cell. The AAV genome is built of single-stranded deoxyribonucleic acid (ssDNA), either positive- or negative-sensed, which is about 4.7 kilobase long. The genome comprises inverted terminal repeats (ITRs) at both ends of the DNA strand, and two open reading frames (ORFs): rep and cap. Rep is composed of four overlapping genes encoding Rep proteins required for the AAV life cycle, and Cap contains overlapping nucleotide sequences of capsid proteins: VP1, VP2 and VP3, which interact together to form a capsid of an icosahedral symmetry. For gene therapy, ITRs seem to be the only sequences required in cis next to the therapeutic gene: structural (cap) and packaging (rep) genes can be delivered in trans. There are currently 11 recognized serotypes of AAV (AAV1-11).

Administration: To provide or give a subject an agent by any effective route. Exemplary routes of administration include, but are not limited to, oral, injection (such as subcutaneous, intramuscular, intradermal, intraperitoneal, intravenous, and intratumoral), sublingual, rectal, transdermal, intranasal, vaginal and inhalation routes. In some embodiments, administration is by injection into the CSF via the intracerebroventricular (ICV) or intrathecal (cisternal or lumbar) route.

Agent: Any polypeptide, compound, small molecule, organic compound, salt, polynucleotide, or other molecule of interest. Agent can include a therapeutic agent, a diagnostic agent or a pharmaceutical agent. A therapeutic agent is a substance that demonstrates some therapeutic effect by restoring or maintaining health, such as by alleviating the symptoms associated with a disease or physiological disorder, or delaying (including preventing) progression or onset of a disease.

Animal: Living multi-cellular vertebrate organisms, a category that includes, for example, mammals and birds. The term mammal includes both human and non-human mammals. Similarly, the term "subject" includes both human and veterinary subjects. An "infant" is a human subject less than one year of age. An adult subject is greater than 18 years of age. Subject may also be 3-9 months of age, 9 to 36 months of age, less than 3 years of age, 3 to 12 years of age, or more than 12 years of age.

Antigen: A compound, composition, or substance that can stimulate an immune response such as the production of antibodies or a T-cell response in an animal, including compositions that are injected or absorbed into an animal. An antigen reacts with the products of specific humoral or cellular immunity, including those induced by heterologous immunogens. The term "antigen" includes all related antigenic epitopes.

Conservative Substitutions: Modifications of a polypeptide that involve the substitution of one or more amino acids for amino acids having similar biochemical properties that do not result in change or loss of a biological or biochemical function of the polypeptide are designated "conservative" substitutions. These conservative substitutions are likely to have minimal impact on the activity of the resultant protein. Table 1 shows amino acids that can be substituted for an original amino acid in a protein, and which are regarded as conservative substitutions.

TABLE

| Original Residue | Conservative Substitutions |
| --- | --- |
| Ala | ser |
| Arg | lys |
| Asn | gln; his |
| Asp | glu |
| Cys | ser |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

One or more conservative changes, or up to ten conservative changes (such as two substituted amino acids, three substituted amino acids, four substituted amino acids, or five substituted amino acids, etc.) can be made in the polypeptide without changing a biochemical function of the protein.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences.

Expression control sequences can include a promoter. Expression control sequences can be operably linked to a nucleic acid molecule encoding a therapeutic protein, and included in an AAV vector.

Heterologous: A heterologous sequence is a sequence that is not normally (in the wild-type sequence) found adjacent to a second sequence. In one embodiment, the sequence is from a different genetic source, such as a virus or organism, than the second sequence.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Immune response: A response of a cell of the immune system, such as a B cell or T cell to a stimulus. In one embodiment, the response is specific for a particular antigen (an "antigen-specific response").

Immunosuppressive agent: A molecule, such as a chemical compound, small molecule, steroid, nucleic acid molecule, or other biological agent, that can decrease an immune response such as an inflammatory reaction. Specific, non-limiting examples of immunosuppressive agents are non-steroidal anti-inflammatory agents, cyclosporine A, FK506, and anti-CD4. Immunosuppressive therapy can include prednisolone, mycophenolate mofetil (MMF) and sirolimus or tacrolimus. In additional examples, the agent is a biological response modifier, such as KINERET® (anakinra), ENBREL® (etanercept), or REMICADE® (infliximab), a disease-modifying antirheumatic drug (DMARD), such as ARAVA® (leflunomide), a nonsteroidal anti-inflammatory drug (NSAID), such as a Cyclo-Oxygenase-2 (COX-2) inhibitor, such as CELEBREX® (celecoxib) and VIOXX® (rofecoxib), or another product, such as HYALGAN® (hyaluronan) and SYNVISC® (hylan G-F20). In some embodiments the immunosuppressive agent crosses the blood brain barrier.

Isolated: An "isolated" biological component (such as a nucleic acid, peptide or protein) has been substantially separated, produced apart from, or purified away from other biological components in the cell of the organism in which the component naturally occurs, i.e., other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids. An isolated cell type has been substantially separated from other cell types, such as a different cell type that occurs in an organ. A purified cell or component can be at least 90%, at least 95%, at least 96%, at least 97%, at least 98%, or at least 99% pure.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes.

Lysosomal storage disease/disorder: Lysosomal storage diseases/disorders are a type of disease involving partial or complete deficiency of a lysosomal hydrolase. This deficiency results in incomplete lysosomal digestion of substrates specific to the hydrolase. Over time, the accumulation of undigested substrate can lead to various abnormalities, including progressive and severe neuro- and muscular-degeneration. (See Settembre et al., *Human Mol. Genet.*, 17:119-129, 2008; Fukuda et al., *Curr. Neurol. Neurosci. Rep.*, 7:71-77, 2007.) The phrase lysosomal storage disorder is synonymous with lysosomal storage disease.

Lysosomal storage disorders include but are not limited to GM2 Gangliosidosis, Alpha-mannosidosis, Aspartylglucosaminuria, Cholesteryl ester storage disease, Chronic Hexosaminidase A Deficiency, Cystinosis, Danon disease, Fabry disease, Farber disease, Fucosidosis, Galactosialidosis, Gaucher Disease, GM1 gangliosidosis, I-Cell disease/Mucolipidosis II, Infantile Free Sialic Acid Storage Disease/ISSD, Juvenile Hexosaminidase A Deficiency, Krabbe disease, Metachromatic Leukodystrophy, Mucopolysaccharidoses disorders (Pseudo-Hurler polydystrophy/Mucolipidosis IIIA, MPSI Hurler Syndrome, MPSI Scheie Syndrome, MPS I Hurler-Scheie Syndrome, MPS II Hunter syndrome, Sanfilippo syndrome, Morquio Type A/MPS IVA, Morquio Type B/MPS IVB, MPS IX Hyaluronidase Deficiency, MPS VI Maroteaux-Lamy, MPS VII Sly Syndrome, Mucolipidosis I/Sialidosis, Mucolipidosis IIIC, Mucolipidosis type IV), Multiple sulfatase deficiency, Niemann-Pick Disease, Neuronal Ceroid Lipofuscinoses (CLN6 disease, Batten-Spielmeyer-Vogt/Juvenile NCL/CLN3 disease, Finnish Variant Late Infantile CLNS, Jansky-Bielschowsky disease/Late infantile CLN2/TPP1 Disease, Kufs/Adult-onset NCL/CLN4 disease, Northern Epilepsy/variant late infantile CLN8, Santavuori-Haltia/Infantile CLN1/PPT disease, Beta-mannosidosis), Pompe disease/Glycogen storage disease type II, Pycnodysostosis, Sandhoff disease, Schindler disease, Salla disease/Sialic Acid Storage Disease, Tay-Sachs/GM2 gangliosidosis, and Wolman disease.

Non lysosomal storage disorders: Non lysosomal storage disorders that can be treated using the methods disclosed herein include, but are not limited to, Spinal Muscular Atrophy (SMA) Types 1, II, III, IV (SMN1, UBA1, DYNC1H1, VAPB genes), X-Linked Myotubular Myopathy (MTM1 gene), Catecholaminergic polymorphic ventricular tachycardia (CASQ2 gene), Achromatopsia (CNGB3, CNGA3, GNAT2, PDE6C genes), Choroidermia (CHM gene), Friedrich's Ataxia CNS (FXN gene), Friedrich's Ataxia Systemic (FXN gene), Adrenoleukodvstrophy (ABCD1 gene), Alzheimer disease (APP, PPARγ genes), Amyotrophic lateral sclerosis (SOD1 gene), Angelman syndrome (UBE3A gene), Ataxia telangiectasia (ATM gene), Charcot-Marie-Tooth syndrome (PMP22 gene), Cockayne syndrome (ERCC6, ERCC8 genes), Deafness (GJB2 gene), Duchenne muscular dystrophy (DMD gene), Epilepsy (SCN1A gene), Fragile X syndrome (FMR1 gene), Huntington disease (HTT gene), Lesch-Nyhan syndrome (HGPRT gene), Maple syrup urine disease (BCKDHA, BCKDHB, DBT genes), Menkes syndrome (ATP7A gene), Myotonic dystrophy (DMPK), Narcolepsy (HLA gene), Neurofibromatosis (NF1 gene), Parkinson's disease (LRRK2, PARK2, PARK7, PINK1, SNCA genes), Phenylketonuria (PAH gene), Prader-Willi syndrome, Refsum disease (PEX7 gene), Rett syndrome (MECP2 gene), Spinocerebellar ataxia (SCA1 gene), Tangier disease (ABCA1 gene), Tuberous sclerosis (TSC1, TSC2 genes), Von Hippel-Lindau syndrome (VHL gene), Williams syndrome (CLIP2, ELN, GTF2I, GTF2IRD1, LIMK1 genes), Wilson's disease (ATP7B gene), or Zellweger syndrome (PEX1 gene).

Mammal: This term includes both human and non-human mammals. Similarly, the term "subject" includes both human and veterinary subjects.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together. This includes nucleic acid vectors comprising an amplified or assembled nucleic acid which can be used to transform a suitable host cell. A host cell that comprises the recombinant nucleic acid is referred to as a "recombinant host cell." The gene is then expressed in the recombinant host cell to produce, such as a "recombinant polypeptide." A recombinant nucleic acid may serve a non-coding function (such as a promoter, origin of replication, ribosome-binding site, etc.) as well.

A first sequence is an "antisense" with respect to a second sequence if a polynucleotide whose sequence is the first sequence specifically hybridizes with a polynucleotide whose sequence is the second sequence.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, for example, by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see for example, *Current Protocols in Molecular Biology* (Ausubel et al., eds 1995 supplement)).

One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, such as version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., J. Mol. Biol. 215:403-410, 1990 and Altschul et al., Nucleic Acids Res. 25:3389-3402, 1977. Software for performing BLAST analyses is publicly available through the National Center for Biotechnology Information. The BLASTN program (for nucleotide sequences) uses as defaults a word length (W) of 11, alignments (B) of 50, expectation (E) of 10, M=5, N=-4, and a comparison of both strands. The BLASTP program (for amino acid sequences) uses as defaults a word length (W) of 3, and expectation (E) of 10, and the BLOSUM62 scoring matrix (see Henikoff & Henikoff, Proc. Natl. Acad. Sci. USA 89:10915, 1989).

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

ORF (open reading frame): A series of nucleotide triplets (codons) coding for amino acids without any termination codons. These sequences are usually translatable into a peptide.

Pharmaceutically acceptable carriers: The pharmaceutically acceptable carriers useful in this invention are conventional. *Remington's Pharmaceutical Sciences*, by E. W. Martin, Mack Publishing Co., Easton, PA, 15th Edition (1975), describes compositions and formulations suitable for pharmaceutical delivery of the AAV vectors herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical agent: A chemical compound or a composition capable of inducing a desired therapeutic or prophylactic effect when properly administered to a subject or a cell. "Incubating" includes a sufficient amount of time for a drug to interact with a cell. "Contacting" includes incubating a drug in solid or in liquid form with a cell.

Polypeptide: A polymer in which the monomers are amino acid residues that are joined together through amide bonds. When the amino acids are alpha-amino acids, either the L-optical isomer or the D-optical isomer can be used, the L-isomers being preferred. The terms "polypeptide" or "protein" as used herein is intended to encompass any amino acid sequence and include modified sequences such as glycoproteins. The term "polypeptide" is specifically intended to cover naturally occurring proteins, as well as those that are recombinantly or synthetically produced.

The term "polypeptide fragment" refers to a portion of a polypeptide which exhibits at least one useful epitope. The term "functional fragments of a polypeptide" refers to all fragments of a polypeptide that retain an activity of the polypeptide. Biologically functional fragments, for example, can vary in size from a polypeptide fragment as small as an epitope capable of binding an antibody molecule to a large polypeptide capable of participating in the characteristic induction or programming of phenotypic changes within a cell. An "epitope" is a region of a polypeptide capable of binding an immunoglobulin generated in response to contact with an antigen. Thus, smaller peptides containing the biological activity of insulin, or conservative variants of the insulin, are thus included as being of use.

The term "soluble" refers to a form of a polypeptide that is not inserted into a cell membrane.

The term "substantially purified polypeptide" as used herein refers to a polypeptide which is substantially free of other proteins, lipids, carbohydrates or other materials with which it is naturally associated. In one embodiment, the polypeptide is at least 50%, for example at least 80% free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated.

Conservative substitutions replace one amino acid with another amino acid that is similar in size, hydrophobicity, etc. Variations in the cDNA sequence that result in amino acid changes, whether conservative or not, should be minimized in order to preserve the functional and immunologic identity of the encoded protein. The immunologic identity of the protein may be assessed by determining if it is recognized by an antibody; a variant that is recognized by such an antibody is immunologically conserved. Any cDNA sequence variant will preferably introduce no more than twenty, and preferably fewer than ten amino acid substitutions into the encoded polypeptide. Variant amino acid sequences may, for example, be 80, 90 or even 95% or 98% identical to the native amino acid sequence.

Polynucleotide: A nucleic acid sequence (such as a linear sequence) of any length. Therefore, a polynucleotide includes oligonucleotides, and also gene sequences found in chromosomes. An "oligonucleotide" is a plurality of joined nucleotides joined by native phosphodiester bonds. An oligonucleotide is a polynucleotide of between 6 and 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Promoter: A promoter is an array of nucleic acid control sequences which direct transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987).

Purified: The term "purified" does not require absolute purity; rather, it is intended as a relative term. Thus, for example, a purified peptide, protein, virus, or other active compound is one that is isolated in whole or in part from naturally associated proteins and other contaminants. In certain embodiments, the term "substantially purified" refers to a peptide, protein, virus or other active compound that has been isolated from a cell, cell culture medium, or other crude preparation and subjected to fractionation to remove various components of the initial preparation, such as proteins, cellular debris, and other components.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, such as by genetic engineering techniques. Similarly, a recombinant protein is one encoded for by a recombinant nucleic acid molecule. In addition, a recombinant virus is a virus comprising sequence (such as genomic sequence) that is non-naturally occurring or made by artificial combination of at least two sequences of different origin. The term "recombinant" also includes nucleic acids, proteins and viruses that have been altered solely by addition, substitution, or deletion of a portion of a natural nucleic acid molecule, protein or virus. As used herein, "recombinant AAV" refers to an AAV particle in which a recombinant nucleic acid molecule (such as a recombinant nucleic acid molecule encoding a therapeutic protein) has been packaged.

Selectable Marker: A gene, RNA, or protein that when expressed, confers upon cells a selectable phenotype, such as resistance to a cytotoxic or cytostatic agent (e.g., antibiotic resistance), nutritional prototrophy, or expression of a particular protein that can be used as a basis to distinguish cells that express the protein from cells that do not. Proteins whose expression can be readily detected such as a fluorescent or luminescent protein or an enzyme that acts on a substrate to produce a colored, fluorescent, or luminescent substance ("detectable markers") constitute a subset of selectable markers. The presence of a selectable marker linked to expression control elements native to a gene that is normally expressed selectively or exclusively in pluripotent cells makes it possible to identify and select specific cells of interest. A variety of selectable marker genes can be used, such as neomycin resistance gene (neo), puromycin resistance gene (puro), guanine phosphoribosyl transferase (gpt), dihydrofolate reductase (DHFR), adenosine deaminase (ada), puromycin-N-acetyltransferase (PAC), hygromycin resistance gene (hyg), multidrug resistance gene (mdr), thymidine kinase (TK), hypoxanthine-guanine phosphoribosyltransferase (HPRT), and hisD gene. Detectable markers include green fluorescent protein (GFP) blue, sapphire, yellow, red, orange, and cyan fluorescent proteins and variants of any of these. Luminescent proteins such as luciferase (e.g., firefly or Renilla luciferase) are also of use. The term "selectable marker" as used herein can refer to a gene or to an expression product of the gene, e.g., an encoded protein.

Sequence identity of amino acid sequences: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, MD) and on the internet, for use in connection with the sequence analysis programs blastp, blastn, blastx, tblastn and tblastx. A description of how to determine sequence identity using this program is available on the NCBI website on the internet.

Homologs and variants of proteins are typically characterized by possession of at least about 75%, for example at least about 80%, 90%, 95%, 96%, 97%, 98% or 99% sequence identity counted over the full length alignment with the amino acid sequence of the antibody using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Subject: Any mammal, such as humans, non-human primates, pigs, sheep, cows, rodents and the like which is to be the recipient of the particular treatment. In two non-limiting examples, a subject is a human subject or a murine subject.

Therapeutic agent: Used in a generic sense, it includes treating agents, prophylactic agents, and replacement agents. A therapeutic agent can be a therapeutic protein. A therapeutic agent, e.g., a therapeutic protein, can be delivered to a subject to prevent, treat, and/or ameliorate a disease. The disease can be a disease of the central nervous system such as a lysosomal storage disorder or a non lysosomal storage disorder.

Therapeutically effective amount: A quantity of a specified pharmaceutical or therapeutic agent (e.g. a recombinant AAV) sufficient to achieve a desired effect in a subject, or in a cell, being treated with the agent, such as increasing insulin production. The effective amount of the agent will be dependent on several factors, including, but not limited to the subject or cells being treated, and the manner of administration of the therapeutic composition.

Transduced and Transformed: A virus or vector "transduces" a cell when it transfers nucleic acid into the cell. A cell is "transformed" or "transfected" by a nucleic acid transduced into the cell when the DNA becomes stably replicated by the cell, either by incorporation of the nucleic acid into the cellular genome, or by episomal replication.

Numerous methods of transfection are known to those skilled in the art, such as: chemical methods (e.g., calcium-phosphate transfection), physical methods (e.g., electroporation, microinjection, particle bombardment), fusion (e.g., liposomes), receptor-mediated endocytosis (e.g., DNA-protein complexes, viral envelope/capsid-DNA complexes) and by biological infection by viruses such as recombinant viruses {Wolff, J. A., ed, Gene Therapeutics, Birkhauser, Boston, USA (1994)}. In the case of infection by retroviruses, the infecting retrovirus particles are absorbed by the target cells, resulting in reverse transcription of the retroviral RNA genome and integration of the resulting provirus into the cellular DNA. Methods for the introduction of genes into the pancreatic endocrine cells are known (e.g. see U.S. Pat. No. 6,110,743, herein incorporated by reference). These methods can be used to transduce a pancreatic endocrine cell produced by the methods described herein, or an artificial islet produced by the methods described herein.

Genetic modification of the target cell is an indicium of successful transfection. "Genetically modified cells" refers to cells whose genotypes have been altered as a result of cellular uptakes of exogenous nucleotide sequence by transfection. A reference to a transfected cell or a genetically modified cell includes both the particular cell into which a vector or polynucleotide is introduced and progeny of that cell.

Transgene: An exogenous gene supplied by a vector.

Vector: A nucleic acid molecule as introduced into a host cell, thereby producing a transformed host cell. A vector may include nucleic acid sequences that permit it to replicate in the host cell, such as an origin of replication. A vector may also include one or more therapeutic genes and/or selectable marker genes and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like. In some embodiments herein, the vector is an AAV vector.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

ssAAV9 Vectors

Disclosed herein are methods and compositions that include one or more vectors, such as a viral vector, for example an adenoviral vector, or an AAV. Defective viruses, that entirely or almost entirely lack viral genes, can be used. Use of defective viral vectors allows for administration to specific cells without concern that the vector can infect other cells. The adenovirus and AAV vectors of use include replication competent, replication deficient, gutless forms thereof. Without being bound by theory, adenovirus vectors are known to exhibit strong expression in vitro, excellent titer, and the ability to transduce dividing and non-dividing cells in vivo (Hitt et al., Adv in Virus Res 55:479-505, 2000). When used in vivo these vectors lead to strong but transient gene expression due to immune responses elicited to the vector backbone. In some non-limiting examples, a vector of use is an attenuated adenovirus vector, such as the vector described by Stratford-Perricaudet et al. (*J. Clin. Invest.*, 90:626-630 1992; La Salle et al., *Science* 259:988-990, 1993); or a defective AAV vector (Samulski et al., *J. Virol.*, 61:3096-3101, 1987; Samulski et al., *J. Virol.*, 63:3822-3828, 1989; Lebkowski et al., *Mol. Cell. Biol.*, 8:3988-3996, 1988).

Recombinant AAV vectors are characterized in that they are capable of directing the expression and the production of the selected transgenic products in targeted cells. Thus, the recombinant vectors comprise at least all of the sequences of AAV essential for encapsidation and the physical structures for infection of target cells.

AAV belongs to the family Parvoviridae and the genus *Dependovirus*. AAV is a small, non-enveloped virus that packages a linear, single-stranded DNA genome. Both sense and antisense strands of AAV DNA are packaged into AAV capsids with equal frequency. In some embodiments the AAV DNA includes a nucleic acid encoding a therapeutic protein. Further provided are recombinant vectors, such as recombinant adenovirus vectors and recombinant adeno-associated virus (rAAV) vectors comprising a nucleic acid molecule disclosed herein. In some embodiments, the AAV is AAV9.

The AAV genome is characterized by two inverted terminal repeats (ITRs) that flank two open reading frames (ORFs). In the AAV2 genome, for example, the first 125 nucleotides of the ITR are a palindrome, which folds upon itself to maximize base pairing and forms a T-shaped hairpin structure. The other 20 bases of the ITR, called the D sequence, remain unpaired. The ITRs are cis-acting sequences important for AAV DNA replication; the ITR is the origin of replication and serves as a primer for second-strand synthesis by DNA polymerase. The double-stranded DNA formed during this synthesis, which is called replicating-form monomer, is used for a second round of self-priming replication and forms a replicating-form dimer. These double-stranded intermediates are processed via a strand displacement mechanism, resulting in single-stranded DNA used for packaging and double-stranded DNA used for transcription. Located within the ITR are the Rep binding elements and a terminal resolution site (TRS). These features are used by the viral regulatory protein Rep during AAV replication to process the double-stranded intermediates. In addition to their role in AAV replication, the ITR is also essential for AAV genome packaging, transcription, negative regulation under non-permissive conditions, and site-specific integration (Daya and Berns, *Clin Microbiol Rev* 21(4):583-593, 2008). In some embodiments, these elements are included in the AAV vector.

The left ORF of AAV contains the Rep gene, which encodes four proteins—Rep78, Rep 68, Rep52 and Rep40. The right ORF contains the Cap gene, which produces three viral capsid proteins (VP1, VP2 and VP3). The AAV capsid contains 60 viral capsid proteins arranged into an icosahedral symmetry. VP1, VP2 and VP3 are present in a 1:1:10 molar ratio (Daya and Berns, *Clin Microbiol Rev* 21(4):583-593, 2008). In some embodiments, these elements are included in the AAV vector, such as an AAV9 vector.

Although AAV infects humans and some other primate species, it is not known to cause disease and elicits a very mild immune response. Gene therapy vectors that utilize AAV can infect both dividing and quiescent cells and persist in an extrachromosomal state without integrating into the genome of the host cell.

AAV possesses several additional desirable features for a gene therapy vector, including the ability to bind and enter target cells, enter the nucleus, the ability to be expressed in the nucleus for a prolonged period of time, and low toxicity. AAV can be used to transfect cells, and suitable vector are known in the art, see for example, U.S. Published Patent Application No. 2014/0037585, incorporated herein by reference. Methods for producing rAAV suitable for gene therapy are well known in the art (see, for example, U.S. Published Patent Application Nos. 2012/0100606; 2012/0135515; 2011/0229971; and 2013/0072548; and Ghosh et al., *Gene Ther* 13(4):321-329, 2006), and can be utilized with the methods disclosed herein.

The vectors of use in the methods disclosed herein can contain nucleic acid sequences encoding an intact AAV capsid which may be from a single AAV serotype (e.g., AAV9, e.g., as disclosed in WO 2005/033321, incorporated herein by reference). As disclosed in U.S. Pat. No. 8,692, 332, vectors of use also can be recombinant, and thus can contain sequences encoding artificial capsids which contain one or more fragments of the AAV9 capsid fused to heterologous AAV or non-AAV capsid proteins (or fragments thereof). These artificial capsid proteins are selected from non-contiguous portions of the AAV9 capsid or from capsids of other AAV serotypes. For example, a rAAV vector may have a capsid protein comprising one or more of the AAV9 capsid regions selected from the VP2 and/or VP3, or from VP1, or fragments thereof selected from amino acids 1 to 184, amino acids 199 to 259; amino acids 274 to 446; amino acids 603 to 659; amino acids 670 to 706; amino acids 724 to 738 of the AAV9 capsid. In another example, it may be desirable to alter the start codon of the VP3 protein to GTG. Alternatively, the rAAV may contain one or more of the AAV serotype 9 capsid protein hypervariable regions, e.g., see WO 2005/033321, incorporated herein by reference.

In some embodiments, a recombinant adeno-associated virus (rAAV) is generated having an AAV serotype 9 capsid. To produce the vector, a host cell which can be cultured that contains a nucleic acid sequence encoding an AAV serotype 9 capsid protein, or fragment thereof, as defined herein; a functional rep gene; a minigene composed of, at a minimum, AAV inverted terminal repeats (ITRs) and a transgene, such as a transgene encoding a therapeutic protein; and sufficient helper functions to permit packaging in the AAV8 capsid protein. The components required to be cultured in the host cell to package an AAV minigene in an AAV capsid may be provided to the host cell in trans. Alternatively, any one or more of the required components (e.g., minigene, rep sequences, cap sequences, and/or helper functions) may be provided by a stable host cell which has been engineered to contain one or more of the required components using methods known to those of skill in the art. In some embodiments, a stable host cell will contain the required component(s) under the control of an inducible promoter. However, the required component(s) can be under the control of a constitutive promoter. Examples of suitable inducible and constitutive promoters are known in the art.

In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contains the rep and/or cap proteins under the control of inducible promoters. Still other stable host cells may be generated by one of skill in the art.

The minigene, rep sequences, cap sequences, and helper functions required for producing a rAAV can be delivered to the packaging host cell in the form of any genetic element which transfer the sequences carried thereon. The selected genetic element may be delivered by any suitable method, including those described herein. The methods used to construct vectors are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present invention. See, e.g., K. Fisher et al, *J. Virol.*, 70:520-532 (1993), U.S. Pat. No. 5,478,745, and PCT Publication No. and WO 2005/033321, incorporated herein by reference. In some embodiments, selected AAV components can be readily isolated using techniques available to those of skill in the art from an AAV serotype, including AAV9. Such AAV may be isolated or obtained from academic, commercial, or public sources (e.g., the American Type Culture Collection, Manassas, Va.). Alternatively, the AAV sequences may be obtained through synthetic or other suitable means by reference to published sequences such as are available in the literature or in databases such as, e.g., GENBANK®.

scAAV Vectors scAAV vectors are disclosed in McCarty et al., 2001, Gene Ther. 8: 1248-1254; Carter PCT Publication No. WO 2001/011034; and Samulski, PCT Publication No. WO 2001/092551, all of which are incorporated by reference herein.

As disclosed in PCT Publication No. "duplexed" DNA parvovirus vectors (as described above) can be advantageously employed for gene delivery. Duplexed parvovirus can provide improved transducing to particle ratios, more rapid transgene expression, a higher level of transgene expression, and/or more persistent transgene expression. The duplexed parvovirus vectors can be used for gene delivery to host cells that are typically refractory to AAV transduction. Thus, duplexed parvovirus vectors, such as AAV9, have a different host range than ssAAV vectors.

These vectors are dimeric self-complementary (sc) polynucleotides (typically, DNA) packaged within a viral capsid, such as a parvovirus capsid, for example an AAV capsid, such as AAV9. In some respects, the viral genome that is packaged within the capsid is essentially a "trapped" replication intermediate that cannot be resolved to produce the plus and minus polarity parvovirus DNA strands. Accordingly, the duplexed parvovirus vectors can circumvent the need for host cell mediated synthesis of complementary DNA inherent in conventional recombinant AAV (ssAAV) vectors.

This result is accomplished by allowing the virus to package essentially dimeric inverted repeats of the single-stranded parvovirus (e.g., ssAAV, such as ssAAV9) vector genome such that both strands, joined at one end, are contained within a single infectious capsid. Upon release from the capsid, the complementary sequences re-anneal to form transcriptionally active double-stranded DNA within the target cell.

The duplexed parvovirus vectors are fundamentally different from conventional parvovirus (e.g., ssAAV such as AAV9) vectors, and from the parent parvovirus (e.g., AAV, such as AAV9), in that the vDNA may form a double-stranded hairpin structure due to intrastrand base pairing, and that both DNA strands are encapsidated. Thus, the duplexed parvovirus vector is functionally similar to double-stranded DNA virus vectors rather than the parvovirus (e.g., ssAAV such as AAV9) from which it was derived.

The viral capsid may be from any parvovirus, either an autonomous parvovirus or dependovirus. Preferably, the viral capsid is an AAV capsid (e.g., an AAV9 capsid). The choice of parvovirus capsid may be based on a number of considerations as known in the art, e.g., the target cell type, the desired level of expression, the nature of the heterologous nucleotide sequence to be expressed, issues related to viral production, and the like. In specific example, the capsid is an AAV9 capsid.

The parvovirus particle may be a "hybrid" particle in which the viral TRs and viral capsid are from different parvoviruses. Preferably, the viral TRs and capsid are from different serotypes of AAV (e.g., as described in international patent publication WO 00/28004, U.S. provisional application No. 60/248,920; and Chao et al., (2000) Molecular Therapy 2:619; the disclosures of which are incorporated herein in their entireties. Likewise, the parvovirus may have a "chimeric" capsid (e.g., containing sequences from different parvoviruses) or a "targeted" capsid (e.g., a directed tropism) as described in these publications. As used herein, a "duplexed parvovirus particle" encompasses hybrid, chimeric and targeted virus particles. Preferably, the duplexed parvovirus particle has an AAV capsid, which may further by a chimeric or targeted capsid, as described above.

A duplexed parvovirus vector can be produced by any suitable method. Preferably, the template for producing the vDNA is one that preferentially gives rise to a duplexed, rather than monomeric vDNA (i.e., the majority of vDNA produced are duplexed) which has the capacity to form a double-stranded vDNA. In some embodiments, at least about 50%, 60%), 70%, 80%, 90%, 95%, 98%, 99% or more of the replication products from the template are duplexed. In one particular embodiment, the template is a DNA molecule comprising one or more terminal repeat (TR) sequences. The template also comprises a modified TR that cannot be resolved (i.e., nicked) by the parvovirus Rep proteins. During replication, the inability of Rep protein to resolve the modified TR will result in a stable intermediate with the two "monomers" covalently attached by the non-resolvable TR. This "duplexed" molecule may be packaged within the parvovirus (AAV) capsid to produce a novel duplexed parvovirus vector, such as a scAAV9 vector.

While not wishing to be held to any particular theory, it is likely that the virion genome is retained in a single-stranded form while packaged within the viral capsid. Upon release from the capsid during viral infection, it appears that the dimeric molecule "snaps back" or anneals to form a double-stranded molecule by intra-strand basepairing, with the non-resolvable TR sequence forming a covalently-closed hairpin structure at one end. This double-stranded vDNA obviates host cell mediated second-strand synthesis, which has been postulated to be a rate-limiting step for AAV transduction.

In some embodiments, the template further comprises a heterologous nucleotide sequence(s) (as described below) to be packaged for delivery to a target cell. According to this particular embodiment, the heterologous nucleotide sequence is located between the viral TRs at either end of the substrate. In further preferred embodiments, the parvovirus (e.g., AAV) cap genes and parvovirus (e.g., AAV) rep genes are deleted from the template (and the vDNA produced therefrom). This configuration maximizes the size of the heterologous nucleic acid sequence(s) that can be carried by the parvovirus capsid.

In one particular embodiment, the template for producing the duplexed parvovirus vectors contains at least one TR at the 5' and 3' ends, flanking a heterologous nucleotide sequence of interest (as described below). The TR at one end of the substrate is non-resolvable, i.e., it cannot be resolved (nicked) by Rep protein. During replication, the inability of Rep protein to resolve one of the TRs will result in a stable intermediate with the two "monomers" covalently attached by the non-functional (i.e., non-resolvable) TR. The heterologous nucleotide sequence may be in either orientation with respect to the non-resolvable TR.

The term "flanked" is not intended to indicate that the sequences are necessarily contiguous. For example, in the example in the previous paragraph, there may be intervening sequences between the heterologous nucleotide sequence and the TR. A sequence that is "flanked" by two other elements, indicates that one element is located 5' to the sequence and the other is located 3' to the sequence; however, there may be intervening sequences therebetween.

According to this embodiment, the template for producing the duplexed parvovirus vDNA is about half of the size of the wild-type parvovirus genome (e.g., AAV) corresponding to the capsid into which the vDNA will be packaged. Alternatively, stated, the template is preferably from about 40% to about 55% of wt, more preferably from about 45% to about 52% of wt. Thus, the duplexed vDNA produced from this template will preferably have a total size that is approximately the size of the wild-type parvovirus genome (e.g., AAV) corresponding to the capsid into which the vDNA will be packaged, e.g., from about 80% to about 105% of wt. In the case of AAV, it is well-known in the art that the AAV capsid disfavors packaging of vDNA that substantially deviate in size from the wt AAV genome. In the case of an AAV capsid, the template is preferably approximately 5.2 kb in size or less. In other embodiments, the template is preferably greater than about 3.6, 3.8, 4.0, 4.2, or 4.4 kb in length and/or less than about 5.4, 5.2, 5.0 or 4.8 kb in length. Alternatively stated, the heterologous nucleotide sequence(s) will typically be less than about 2.5 kb in length (more preferably less than about 2.4 kb, still more preferably less than about 2.2 kb in length, yet more preferably less than about 2.1 kb in length) to facilitate packaging of the duplexed template by the parvovirus (e.g., AAV) capsid. In another particular embodiment, the template itself is duplexed, i.e., is a dimeric self-complementary molecule.

According to this embodiment, the template comprises a resolvable TR at either end. The template further comprises a centrally-located non-resolvable TR (as described above). In other words, each half of the template on either side of the non-resolvable TR is approximately the same length. Each half of the template (i.e., between the resolvable and non-resolvable TR) comprises one or more heterologous nucleotide sequence(s) of interest. The heterologous nucleotide sequence(s) in each half of the molecule is flanked by a resolvable TR and the central non-resolvable TR.

The sequences in either half of the template are substantially complementary (i.e., at least about 90%, 95%, 98%, 99% nucleotide sequence complementarity or more), so that the replication products from the template may form double-stranded molecules due to base-pairing between the complementary sequences. In other words, the template is essentially an inverted repeat with the two halves joined by the non-resolvable TR.

In some non-limiting examples, the heterologous nucleotide sequence(s) in each half of the template are essentially completely self-complementary (i.e., contains an insignificant number of mis-matched bases, or even no mismatched bases). In additional non-limiting examples, the two halves of the nucleotide sequence are essentially completely self-complementary.

According to this embodiment, the template (and the vDNA produced therefrom) is preferably approximately the same size as the wt genome naturally encapsulated by the parvovirus capsid (e.g., AAV), i.e., to facilitate efficient packaging into the parvovirus capsid. For example, in the case of an AAV capsid, the template is preferably approximately the size of the wild type (wt) AAV genome. In particular embodiments, the template is approximately 5.2 kb in size or less. In other embodiments, the template is preferably greater than about 3.6, 3.8, 4.0, 4.2, or 4.4 kb in length and/or less than about 5.4, 5.2, 5.0 or 4.8 kb in length. As an alternative statement, the template is preferably in the range of 80% to 105% of the wildtype parvovirus genome (e.g., AAV).

The TR(s) (resolvable and non-resolvable) are preferably AAV sequences, with serotypes 1, 2, 3, 4, 5 and 6 being preferred. The term "terminal repeat" includes synthetic sequences that function as an AAV inverted terminal repeat, such as the "double-D sequence" as described in U.S. Pat. No. 5,478,745 to Samulski et al., the disclosure of which is incorporated in its entirety herein by reference. Resolvable AAV TRs need not have a wild-type TR sequence (e.g., a wild-type sequence may be altered by insertion, deletion, truncation or missense mutations), as long as the TR mediates the desired functions, e.g., virus packaging, integration, and/or provirus rescue, and the like. Typically, but not necessarily, the TRs are from the same parvovirus, e.g., both TR sequences are from AAV2.

The viral Rep protein(s) used for producing the duplexed vectors are selected with consideration for the source of the viral TRs. For example, the AAV5 TR interacts more efficiently with the AAV5 Rep protein.

The genomic sequences of the various autonomous parvoviruses and the different serotypes of AAV, as well as the sequences of the TRs, capsid subunits, and Rep proteins are known in the art. Such sequences may be found in the literature or in public databases such as GENBANK®. See, e.g., GENBANK® Accession Numbers NC 002077, NC 001863, NC 001862, NC 001829, NC 001729, NC 001701, NC 001510, NC 001401, AF063497, U89790, AF043303, AF028705, AF028704, J02275, J01901, J02275, X01457, AF288061, AH009962, AY028226, AY028223, NC 001358, NC 001540; the disclosures of which are incorporated herein in their entirety. See also, e.g., Chiorini etal., (1999) J. Virology 73:1309; Xiao et al., (1999) J. Virology 73:3994; Muramatsu et al., (1996) Virology 221:208; international patent publications WO 00/28061, WO 99/61601, WO 98/11244; U.S. Pat. No. 6,156,303; the disclosures of which are incorporated herein in their entirety.

The non-resolvable TR may be produced by any method known in the art. For example, insertion into the TR will displace the nicking site (i.e., trs) and result in a non-resolvable TR. The designation of the various regions or elements within the TR are known in the art. An illustration of the regions within the AAV TR is provided in FIG. 6 (see also, BERNARD N. FIELDS et al., VIROLOGY, volume 2, chapter 69, FIG. 5, 3d ed., Lippincott-Raven Publishers). The insertion is preferably made into the sequence of the terminal resolution site (trs). Alternatively, the insertion may be made at a site between the Rep Binding Element (RBE) within the A element and the trs in the D element (see FIG. 6). The core sequence of the AAV trs site is known in the art and has been described by Snyder et al., (1990) Cell 60:105; Snyder et al., (1993) J. Virology 67:6096; Brister & Muzyczka, (2000) J. Virology 74:7762; Brister & Muzyczka, (1999) J. Virology 73:9325 (the disclosures of which are hereby incorporated by reference in their entireties). For example, Brister & Muzyczka, (1999) J. Virology 73:9325 describes a core trs sequence of 3'-CCGGT/TG-5* in the D element. Snyder et al., (1993) J. Virology 67:6096 identified the minimum trs sequence as 3'-GGT/TGA-5', which substantially overlaps the sequence identified by Brister & Muzyczka. Preferably, the insertion is in the region of the trs site. The insertion may be of any suitable length that will reduce or substantially eliminate (e.g., by 60%, 70%), 80%. 90%, 95% or greater) resolution of the TR. In some embodiments, the insertion is at least about 3, 4, 5, 6, 10, 15, 20 or 30 nucleotides or more. There are no particular upper limits to the size of the inserted sequence, as long as suitable levels of viral replication and packaging are achieved (e.g., the insertion can be as long as 50, 100, 200 or 500 nucleotides or longer).

In another embodiment, the TR may be rendered non-resolvable by deletion of the trs site. The deletions may extend 1, 3, 5, 8, 10, 15, 20, 30 nucleotides or more beyond the trs site, as long as the template retains the desired functions. In addition to the trs site, some or all of the D element may be deleted. Deletions may further extend into the A element, however those skilled in the art will appreciate that it may be advantageous to retain the RBE in the A element, e.g., to facilitate efficient packaging.

Deletions into the A element may be 2, 3, 4, 5, 8, 10, or 15 nucleotides in length or more, as long as the non-resolvable TR retains any other desired functions. It is further preferred that some or all of the parvovirus (e.g., AAV) sequences going beyond the D element outside the TR sequence (e.g., to the right of the D element in FIG. 6) be deleted to prevent gene conversion to correct the altered TR.

As still a further alternative, the sequence at the nicking site may be mutated so that resolution by Rep protein is reduced or substantially eliminated. For example, A and/or C bases may be substituted for G and/or T bases at or near the nicking site. The effects of substitutions at the terminal resolution site on Rep cleavage have been described by Brister & Muzyczka, (1999) J. Virology 73:9325 (the disclosure of which is hereby incorporated by reference). As a further alternative, nucleotide substitutions in the regions surrounding the nicking site, which have been postulated to form a stem-loop structure, may also be used to reduce Rep cleavage at the terminal resolution site.

Those skilled in the art will appreciate that the alterations in the non-resolvable TR may be selected so as to maintain desired functions, if any, of the altered TR (e.g., packaging, Rep recognition, site-specific integration, and the like).

In more preferred embodiments, the TR will be resistant to the process of gene conversion as described by Samulski et al., (1983) Cell 33:135. Gene conversion at the non-resolvable TR will restore the trs site, which will generate a resolvable TR and result in an increase in the frequency of monomeric replication products. Gene conversion results by homologous recombination between the resolvable TR and the altered TR.

One strategy to reduce gene conversion is to produce virus using a cell line (preferably, mammalian) that is defective for DNA repair, as known in the art, as these cell lines will be impaired in their ability to correct the mutations introduced into the viral template. Alternatively, templates that have a substantially reduced rate of gene conversion can be generated by introducing a region of non-homology into the non-resolvable TR. Non-homology in the region surrounding the trs element between the non-resolvable TR and the unaltered TR on the template will reduce or even substantially eliminate gene conversion.

Any suitable insertion or deletion may be introduced into the non-resolvable TR to generate a region of non-homology, as long as gene conversion is reduced or substantially eliminated. Strategies that employ deletions to create non-homology are preferred. It is further preferred that the deletion does not unduly impair replication and packaging of the template. In the case of a deletion, the same deletion may suffice to impair resolution of the trs site as well as to reduce gene conversion.

As a further alternative, gene conversion may be reduced by insertions into the non-resolvable TR or, alternatively, into the A element between the RBE and the trs site. The insertion is typically at least about 3, 4, 5, 6, 10, 15, 20 or 30 nucleotides or more nucleotides in length. There is no particular upper limit to the size of the inserted sequence, which may be as long as 50, 100, 200 or 500 nucleotides or longer, however, it is preferred that the insertion does not unduly impair replication and packaging of the template.

In alternative embodiments, the non-resolvable TR may be a naturally-occurring TR (or altered form thereof) that is non-resolvable under the conditions used. For example, the non-resolvable TR may not be recognized by the Rep proteins used to produce the vDNA from the template. To illustrate, the non-resolvable TR may be an autonomous parvovirus sequence that is not recognized by AAV Rep proteins. As a yet further alternative, the non-resolvable sequence may be any inverted repeat sequence that forms a hairpin structure and cannot be cleaved by the Rep proteins.

As still a further alternative, a half-genome size template may be used to produce a parvovirus particle carrying a duplexed vDNA, produced from a half-genome sized template, as described in the Examples herein and by Hirata & Russell, (2000) J. Virology 74:4612. This report describes packaging of paired monomers and transient RF intermediates when AAV genomes were reduced to less than half-size of the wtAAV genome (<2.5 kb). These investigators found that monomeric genomes were the preferred substrate for gene correction by homologous recombination, and that duplexed genomes functioned less well than did monomeric genomes in this assay. This report did not investigate or suggest the use of duplexed genomes as vectors for gene delivery.

In some embodiments, the template will be approximately one-half of the size of the vDNA that can be packaged by the parvovirus capsid. For example, for an AAV capsid, the template is preferably approximately one-half of the wt AAV genome in length, as described above. The template (as described above) is replicated to produce a duplexed vector genome (vDNA), which is capable of forming a double-stranded DNA under appropriate conditions. The duplexed molecule is substantially self-complementary so as to be capable of forming a double-stranded viral DNA (i.e., at least 90%, 95%, 98%, 99%) nucleotide sequence complementarity or more). Base-pairing between individual nucleotide bases or polynucleotide sequences is well-understood in the art. Preferably, the duplexed parvovirus viral DNA is essentially completely self-complementary (i.e., contains no or an insignificant number of mis-matched bases). In particular, it is preferred that the heterologous nucleotide sequence(s) (e.g., the sequences to be transcribed by the cell) are essentially completely self-complementary.

In general, the duplexed parvoviruses may contain non-complementarity to the extent that expression of the heterologous nucleotide sequence(s) from the duplexed parvovirus vector is more efficient than from a corresponding monomeric vector.

The duplexed parvoviruses provide the host cell with a double-stranded molecule that addresses the need for the host cell to convert the single-stranded rAAV vDNA into a double-stranded DNA. The presence of any substantial regions of non-complementarity within the virion DNA, in particular, within the heterologous nucleotide sequence(s) will likely be recognized by the host cell, and will result in DNA repair mechanisms being recruited to correct the mismatched bases, thereby counteracting the advantageous characteristics of the duplexed parvovirus vectors, e.g., the vectors reduce or eliminate the need for the host cell to process the viral template.

Lysosomal Storage Disorders and Transgenes

Disclosed herein is the surprising discovery of the different expression pattern following intracerebroventricular administration of scAAV9 and ssAAV9. In some embodiments, intracerebrovetircular administration of scAAV9 or ssAAV9 can be used to treat a lysomsomal storage disorder.

Lysosomal storage disorders are a type of disease involving partial or complete deficiency of a lysosomal hydrolase. This deficiency results in incomplete lysosomal digestion of substrates specific to the hydrolase. Over time, the accumulation of undigested substrate can lead to various abnormalities, including progressive and severe neuro- and muscular-degeneration (see Settembre et al., *Human Mol. Genet.*, 17:119-129, 2008; Fukuda et al., *Curr. Neurol. Neurosci. Rep.*, 7:71-77 2007).

The deficiency in the lysosomal protein usually results in harmful accumulation of a metabolite. For example, in Hurler, Hunter's (Mucopolysaccharidosis II), Morquio's, and Sanfilippo's syndromes, there is an accumulation of mucopolysaccharides; in Tay-Sachs, Gaucher, Krabbe, Niemann-Pick, and Fabry syndromes, there is an accumulation of sphingolipids; and in fucosidosis and mannosidosis, there is an accumulation of fucose-containing sphingolipids and glycoprotein fragments, and of mannose-containing oligosaccharides, respectively.

Enzyme replacement therapy (ERT) as treatment for lysosomal storage diseases (LSDs) was suggested as long ago as 1966 by De Duve and Wattiaux. However, it took >35 years to demonstrate the safety and effectiveness of ERT for a lysosomal storage disorder (type 1 Gaucher disease) (Charrow, *Expert Opin. Biol. Ther.*, 9:121-31, 2009). The principles elaborated in the development of the treatment of Gaucher disease were subsequently applied to the development of ERT of other LSDs. The safety and effectiveness of ERT for Fabry disease (Zarate and Hopkin, *Lancet*, 18:1427-1435, 2008), mucopolysaccharidoses (MPS) I, MPS II and MPS VI (Clarke, *Expert Rev. Mol. Med.*, 10:e1, 2008), as well as for Pompe's disease (van der Beek, *Acta Neurol. Belg.*, 106:82-86, 2006) have been demonstrated in well designed clinical trials, and the treatments are now commercially available (see e.g., Rohrbach and Clarke, *Drugs*, 67:2697-2716, 2007 and Burrow et al., *Curr. Opin. Pediatr.*, 19:628-625, 2007 for review). However, some manifestations of the LSD will not respond to ERT treatment. Additionally, the long-term effectiveness of most of the treatments has not yet been established.

Pompe disease (a.k.a. Glycogenosis type II (GSDII)) is a type of lysosomal storage disorder caused by partial or complete deficiency of lysosomal acid α-glucosidase (GAA). GAA is responsible for the breakdown of glycogen within lysosomes, and enzyme deficiency results in accumulation of glycogen, primarily in skeletal and cardiac muscle. The disease has been separated into two broad categories: infantile onset and late-onset. Patients with the infantile form generally die within the first year of life due to cardiorespiratory failure. The late-onset form presents any time after infancy with generally no cardiac involvement but progressive skeletal muscle myopathy, leading to eventual respiratory failure. It is estimated that 1 in 40,000 individuals have some form of Pompe disease. For a review, see Fukuda et al., *Curr. Neurol. Neurosci. Rep.*, 7:71-77 2007.

ERT treatment of Pompe disease involves intravenous injections of a recombinant GAA (rhGAA) precursor containing mannose-6-phosphate (M6P) groups. Genzyme Corporation sells the commercially available replacement enzyme under the trade name Myozyme® (injectable alglucosidase alfa) and Lumizyme®. The M6P groups bind to cation-independent mannose-6-phoshate receptor (CI-MPR) on the cell surface. The CI-MPR/rhGAA complex internalizes from the cell surface in transport vesicles that fuse with endosomes. In the acidic pH of late endosomes, the rhGAA dissociates from CI-MPR and is transported to the lysosomes, where it rescues the GAA deficiency. ERT for Pompe disease is reviewed, for instance, by Fukuda et al. (*Curr. Neurol. Neurosci. Rep.*, 7:71-77, 2007).

ERT for Pompe disease is effective for glycogen clearance in cardiac muscle, but less effective for glycogen clearance from skeletal muscle (Raben et al., *Acta Myologica*, 26:45-48, 2007). Similarly, in genetically engineered mice that lack expression of GAA (a mouse model of Pompe disease), ERT is effective in clearing gylcogen from type I muscle fibers, but not type II muscle fibers, which predominate in skeletal muscle (Raben et al., *Molecular Therapy*, 11:48-56, 2005).

Fabry disease is an X-linked, hereditary, lysosomal storage disease caused by deficiency of the enzyme alpha-galactosidase A, which results in the accumulation of the neutral glycosphingolipid globotriaosylceramide (Gb3) in the walls of small blood vessels, nerves, dorsal root ganglia, renal glomerular and tubular epithelial cells, and cardiomyocytes. It is a complex, multisystem disorder that is characterized clinically by chronic pain and acroparesthesia, gastrointestinal disturbances, characteristic skin lesions (angiokeratomata), progressive renal impairment, cardiomyopathy, and stroke. Enzyme replacement therapy with intravenous infusions of recombinant human alpha-galactosidase A consistently decreases Gb3 levels in plasma and clears lysosomal inclusions from vascular endothelial cells. The effects of ERT on other tissues are not as obvious, suggesting that treatment must be initiated early in the course of the disease to be optimally effective or that some complications of the disease are not responsive to enzymes delivered intravenously (see Clarke, *Ann. Intern Med.*, 20:425-433, 2007 and Desnick, *Ann. Intern. Med.*, 138:338-346, 2003 for review).

Gaucher disease is an inherited disorder caused by deficient activity of the enzyme glucocerebrosidase, found mainly in lysosomes. This results in an accumulation of glucocerebroside in the lysosomes of macrophages, predominantly in the reticuloendothelial system. Consequences of this abnormal storage include visceral problems such as hepatomegaly, splenomegaly, anaemia and thrombocytopenia causing fatigue, discomfort, infections, bleeding and bruising; bone problems such as pain (acute or chronic) and bone crises, and avascular necrosis; and other problems such as lung disease, impaired growth and delayed puberty. The severity of symptoms and rate of progression vary considerably from patient to patient and range from asymptomatic to severe with early death. Gaucher disease is classified into three subtypes by clinical features. Type I can present at any age and has predominantly visceral symptoms without neurological effects. Type II causes severe progressive brain disease and death occurs in infancy. Type III presents in childhood and has neurological and visceral symptoms. See Connock et al., *Health Technology Assessment*, 10: iii-136, 2004; and Beutler, *PLoS Med.*, 1:e21, 2004.

Imiglucerase (available commercially as CEREZYME™ from Genzyme Corporation) is a recombinant enzyme modified to contain mannose to enhance its uptake into cells and delivery to the lysosomes. It is given intravenously to replace the defective enzyme and is licensed for use in symptomatic type I disease and to treat the visceral symptoms of type III disease. Intravenous CEREZYME® cannot cross the blood-brain barrier and is not effective for neurological manifestations. However, a transgene encoding imiglucerase could be included in a scAAV9 or ssAAV9 vector and used in the disclosed methods.

Hurler syndrome, also known as mucopolysaccharidosis type I (MPS I), Hurler disease or gargoylism, is a genetic disorder that results in the buildup of mucopolysaccharides due to a deficiency of alpha-L iduronidase, an enzyme responsible for the degradation of mucopolysaccharides in lysosomes (Tolar and Orchard, *Biologics.*, 2:743-751, 2008). Without this enzyme, a buildup of heparan sulfate and dermatan sulfate occurs in the body. Symptoms appear during childhood and early death can occur due to organ damage. MPS I is divided into three subtypes based on severity of symptoms. All three types result from an absence of, or insufficient levels of, the enzyme α-L-iduronidase. MPS I H or Hurler syndrome is the most severe of the MPS I subtypes. The other two types are MPS I S or Scheie syndrome and MPS I H-S or Hurler-Scheie syndrome. Recombinant alpha-L-iduronidase (IDUA) is used for ERT for MPS I and reduces IDUA substrate accumulation in MPS I Subjects (Tolar and Orchard, *Biologics.*, 2:743-751, 2008). These transgenes can be included in a scAAV9 or ssAAV9 vector and used in the disclosed methods.

Hunter Syndrome (Mucopolysaccharidosis II) is a mucopolysaccharidosis (MPS) that is one of a family of inherited disorders of glycosaminoglycan (GAG) catabolism (Neufeld et al., *The Metabolic and Molecular Bases of Inherited Disease*. New York, N.Y.: McGraw-Hill; 3421-3452, 2001). Hunter syndrome is a rare, X-linked disorder. Each MPS is caused by a deficiency in the activity of the distinct lysosomal enzymes required for the stepwise degradation of the GAGs dermatan sulfate, heparan sulfate, keratan sulfate, and chondroitin sulfate (Neufeld et al., *The Metabolic and Molecular Bases of Inherited Disease*. New York, N.Y.: McGraw-Hill; 3421-3452, 2001). In affected patients, undegraded or partially degraded GAG accumulates within lysosomes and is excreted in excess in the urine (Dorfman et al., *Proc Natl Acad Sci USA*, 43:443-4462, 1957). It is the accumulation, or storage, of GAG within lysosomes that contributes to the signs and symptoms of these disorders. MPS is chronic and progressive. The biochemical cause of Hunter syndrome is a deficiency in the activity of the lysosomal enzyme, iduronate-2-sulfatase (I2S), which catalyzes the removal of the sulfate group at the 2 position of L-iduronic acid in dermatan sulfate and heparin sulfate (Bach et al., *Proc. Natl. Acad. Sci. USA.*, 70:2134-2213, 1973; Neufeld et al., *The Metabolic and Molecular Bases of Inherited Disease*. New York, N.Y.: McGraw-Hill; 3421-3452, 2001). Thus, this gene can be included in a scAAV9 or ssAAV9 vector and used in the disclosed methods.

Idursulfase (Elaprase, Shire Human Genetic Therapies, Inc, Cambridge, Mass.) is a recombinant human I2S produced in a human cell line that is approved in the United States and the European Union for the treatment of Hunter syndrome. A Randomized, placebo-controlled, double-blind clinical trial shows a clinical benefit in patients treated with idursulfase compared with patients treated with placebo. Patients treated with idursulfase demonstrate a statistically significant improvement rate compared with placebo. In addition, urine GAG excretion and liver and spleen volumes were significantly reduced from baseline by both idursulfase dosing regimens. Idursulfase was generally well tolerated, and the majority of treatment-emergent adverse events were consistent with the natural history of untreated Hunter syndrome. On the basis of the larger clinical response in the weekly group compared with the EOW group, idursulfase was approved for the treatment of MPS II in both the United States and European Union at a dose of 0.5 mg/kg weekly (see Muenzer et al., *Genet. Med.*, 8:465-473, 2006).

Mucopolysaccharidosis IV (MPS IV; a.k.a. Morquio syndrome), is an autosomal recessive lysosomal storage disorder involving accumulation of keratan sulfate (Tomatsu et al., *Hum. Mol. Genet.*, 17:815-824, 2007). Two forms are recognized: Type A is a deficiency of the enzyme N-acetyl-galactosamine-6-sulfate sulfatase; Type B is a deficiency of the enzyme beta-galactosidase. Clinical features are similar in both types but appear milder in Type B. Onset is between ages 1 and 3. Neurological complications include spinal nerve and nerve root compression resulting from extreme, progressive skeletal changes, particularly in the ribs and chest; conductive and/or neurosensitive loss of hearing and clouded corneas. Intelligence is normal unless hydrocephalus develops and is not treated. Physical growth slows and often stops between the ages of 4-8. Skeletal abnormalities include a bell-shaped chest, a flattening or curvature of the spine, shortened long bones, and dysplasia of the hips, knees, ankles, and wrists. ERT with recombinant N-acetyl-galactosamine-6-sulfate sulfatase has been used to treat a mouse model of MPSIV that lacks expression of N-acetyl-galactosamine-6-sulfate sulfatase (Tomatsu et al., *Hum. Mol. Genet.*, 17:815-824, 2007).

Any of these lysosomal storage disorders can be treated using the methods disclosed herein. The treatment can include enzyme replacement therapy as well as ICV administration of a ssAAV9 and/or an scAAV9 vector encoding a therapeutic gene.

Non Lysosomal Storage Disorders and Transgenes

Non lysosomal storage disorders that can be treated using the methods disclosed herein include, but are not limited to, Spinal Muscular Atrophy (SMA) Types 1, II, III, IV (SMN1, UBA1, DYNC1H1, VAPB genes), X-Linked Myotubular Myopathy (MTM1 gene), Catecholaminergic polymorphic ventricular tachycardia (CASQ2 gene), Achromatopsia (CNGB3, CNGA3, GNAT2, PDE6C genes), Choroidermia (CHM gene), Friedrich's Ataxia CNS (FXN gene), Friedrich's Ataxia Systemic (FXN gene), Adrenoleukodystrophy (ABCD1 gene), Alzheimer disease (APP, PPARγ genes), Amyotrophic lateral sclerosis (SOD1 gene), Angelman syndrome (UBE3A gene), Ataxia telangiectasia (ATM gene), Charcot-Marie-Tooth syndrome (PMP22 gene), Cockayne syndrome (ERCC6, ERCC8 genes), Deafness (GJB2 gene), Duchenne muscular dystrophy (DMD gene), Epilepsy (SCN1A gene), Fragile X syndrome (FMR1 gene), Huntington disease (HTT gene), Lesch-Nyhan syndrome (HGPRT gene), Maple syrup urine disease (BCKDHA, BCKDHB, DBT genes), Menkes syndrome (ATP7A gene), Myotonic dystrophy (DMPK), Narcolepsy (HLA gene), Neurofibromatosis (NF1 gene), Parkinson's disease (LRRK2, PARK2, PARK7, PINK1, SNCA genes), Phenylketonuria (PAH gene), Prader-Willi syndrome, Refsum disease (PEX7 gene), Rett syndrome (MECP2 gene), Spinocerebellar ataxia (SCA1 gene), Tangier disease (ABCA1 gene), Tuberous sclerosis (TSC1, TSC2 genes), Von Hippel-Lindau syndrome (VHL gene), Williams syndrome (CLIP2, ELN, GTF2I, GTF2IRD1, LIMK1 genes), Wilson's disease (ATP7B gene), or Zellweger syndrome (PEX1 gene).

Immunosuppressive Agents

In some embodiments, the immunosuppressive agent is a biological response modifier, such as KINERET® (anakinra), ENBREL® (etanercept), or REMICADE® (infliximab), a disease-modifying antirheumatic drug (DMARD), such as ARAVA® (leflunomide), a steroid, such as prednisone or cortisone, immunosuppressive agents such as mycophenolate mofetil (MMF), macrolide inhibitors of IL-2 such as sirolimus (rapamycin), or tacrolimus, a nonsteroidal anti-inflammatory drug (NSAID), such as celecoxib, choline magnesium trisalicylate, diclofenac, diclofenac potassium, diclofenac XR, diflunisal, etodolac, etodolac ER, fenoprofen, flurbiprofen oral, ibuprofen, indomethacin, indomethacin SR, indomethacin suppositories, ketoprofen, ketoprofen ER, meclofenamate, meloxicam, nabumetone, naproxen, naproxen CR, naproxen ER, oxaprozin, piroxicam, rofecoxib, salsalate, sulindac, or tolmetin sodium, or another product, such as HYALGAN® (hyaluronan) or SYNVISC® (hylan G-F20).

Immunosuppressive therapy can include treatment with prednisolone, mycophenolate mofetil (MMF) and sirolimus or tacrolimus.

In some embodiments, the immunosuppressive agent does not cross the blood brain barrier.

EXAMPLES

Gene therapy for the central nervous system is poised to become a powerful treatment for numerous neurological disorders. Adeno-associated viral vectors based on serotype 9 (AAV9) are strong candidates for delivering gene-based therapies throughout the brain and spinal cord when administered intravenously, intrathecally, intracisternally, and intracerebroventricularly (ICV). Previous studies of ICV-delivered self-complimentary AAV9 have been performed in neonatal mice with delivery of a single dose. However, before clinical trials can be considered, more information is required about the dose-response relationship for transduction efficiency in adult animals. As disclosed below, three doses of self-complementary AAV9 were administered to adult rats. High levels of transduction were observed in the hippocampus, cerebellum, and cerebral cortex, and transduction increased with increasing dosage. Both neurons and astrocytes were transduced. There was no evidence of astrocytosis at the doses tested. Preliminary results from pigs receiving ICV self-complementary AAV9 are also presented. The results of these dosing studies in large animal models provide evidence that the methods are effective clinically.

Example 1

Materials & Methods

Vector: Self-complimentary AAV9 (scAAV9) was utilized. The expression vector uses a proprietary mini-chicken β-actin promoter to drive expression of an enhanced green fluorescent protein (GFP) cDNA. In the rat studies, the vector titer $1.2 \times 10^{13}$ vector genomes (vg) per ml. For the pig study scAAV9 expressing GFP from a cytomegalovirus enhancer/chicken β-actin promoter was purchased from Nationwide Children's Hospital's vector core. It was used at a concentration of $1.34 \times 10^{13}$ vg/ml.

Animal surgery: Male Sprague-Dawley rats were obtained from Charles River Labs (catalog number 400, 276-300 g body weight) and allowed to acclimate to the animal facility for two to seven days before surgery was performed. Rats were maintained on a 12:12 hour light-dark cycle with food (Labdiet 5001; Labdiet, St. Louis, Mo.) and tap water provided ad libitum. Individual rats were randomly assigned to the treatment groups described below.

Rats were anesthetized and maintained on 2% isofluorane/98% oxygen throughout the procedure (0.6 L/min). The head was immobilized in a stereotactic frame using a nose cone and ear bars. The top of the head was shaved and sterilized with ethanol and betadine, and a sterile drape was applied around the surgical site. Lidocaine was administered subcutaneously, and buprinorphine (0.1 mg/kg) was administered to alleviate post-operative pain. Using a dental drill, a burr hole was drilled through the skull unilaterally at a position 0.8 mm posterior to Bregma and 1.6 mm lateral from midline. Vector was delivered using a Hamilton syringe with a 27 gauge needle affixed to a micromanipulator. Three doses were evaluated: 3.1 ul (low dose, $3.7 \times 10^{10}$ vg; n=3), 15.5 ul (medium dose, $1.9 \times 10^{11}$ vg; n=2), and 77.5 ul (high dose, $9.3 \times 10^{11}$ vg; n=3). In addition, a fourth cohort was included that used the lowest dose of virus ($3.7 \times 10^{10}$ vg) delivered at the highest volume (77.5 ul) to account for differences in delivery volume (low dose/high volume; n=3). Vector was injected at a rate of ~25 ul/min, controlled by a manual injection knob on the micromanipulator. The needle was left in place for one minute following the injection and then slowly withdrawn. The skin was closed and the animal was kept warm during recovery. After three weeks, the animals were euthanized, perfused with saline followed by 4% paraformaldehyde (PFA). Brain, spinal cord, and liver tissue were postfixed in 4% PFA overnight followed by cryopreservation in sucrose. Tissue was frozen on dry ice and stored at −80 C prior to sectioning.

Farm pigs (30 kg) were obtained from Palmetto Research Swine (Reevesville, S.C.). Animals were sedated with 0.8 mg/kg acepromazine, 33 mg/kg ketamine, and 0.04 mg/kg atropine. Anesthesia was maintained using isoflurane. Pain was managed with a fetanyl patch (100 ug/hr for three days). The skin was incised in a paramedian orientation and dissection was carried down to the occipital keel. A burr hole was drilled ~1 cm posterior and medial to the ipsilateral supraorbital foramen with a high-speed Midas Legend. The dura was punctured with an 18 gauge needle. A proximal ventriculoperitoneal shunt catheter was inserted ~2.5 cm into the brain at a posterior and slightly medial direction toward the ipsilateral frontal horn of the right lateral ventricle until it was felt penetrating the ventricle. Correct placement of the needle was determined by observing flow of cerebrospinal fluid (CSF) once the stylet was withdrawn. Placement was confirmed by contrast ventriculography using Omnipaque-300 radiocontrast dye. The catheter was advanced an additional 1 cm, and 3 ml of CSF were removed. 1.5 to 4.5 ml of AAV9-GFP ($1.34 \times 10^{13}$ vg/ml in 20 mM Tris pH 8.0, 1 mM MgCl2, 200 mM NaCl+0.001% Pluronic F68) were delivered over 10 minutes using a MINJ-PD pump (Tritech Research, Los Angeles, Calif.). The catheter left in place for an additional 15 minutes and then was removed. A small piece of gelfoam was placed over the parenchymal penetration site and the burr hole was sealed with bone wax. The skin was closed with interrupted 3-0 Vicryl suture followed by running 2-0 Ethilon. After 22 days, the animals received intravenous heparin followed by perfusion with saline and 4% PFA and the brains were harvested. Tissue was cryopreserved in 30% sucrose prior to sectioning.

Histology: 40 μm coronal sections were cut on a Leica CM1950 cryostat. Primary antibodies for GFP (Millipore AB3080P, Billerica, Mass.), GFAP (Millipore MAB360), NeuN (Millipore MAB377), S100β (Millipore MAB079-1), Fox-2 (Abcam ab167282, Cambridge, Mass.), Calbindin (Sigma C9848, Saint Louis, Mo.) and GAD67 (Millipore MAB5406) were used at 1:500 for immunohistochemistry. Antigen retrieval for S100β and Fox-2 was performed using citrate buffer (10 mM sodium citrate, pH 6.0) for 20 minutes at 52 C or 95 C, respectively. For fluorescent microscopy, an Alexa Fluor® 488-conjugated goat anti-rabbit secondary (Life Technologies A11070, Grand Island, N.Y.) was used to detect GFP and an Alexa Fluor® 596-conjugated goat anti-mouse secondary (Life Technologies A11032) was used to detect the cell type markers at a 1:500 dilution. For chromogenic detection of GFP+ cells, a biotin-conjugated goat anti-rabbit secondary (Jackson Immunoresearch 111-065-144, West Grove, Pa.) was used at a 1:250 dilution followed by a Vector ABC kit and HRP detection system (Vector, Burlingame, Calif.). Slides were imaged with a Nikon (Tokyo, Japan) Eclipse E400 microscope with fluorescence filters (UV-2E/C, B-2E/C, and G-2E/C) and a Nikon Digital Sight controller with DS-Qi1Mc and DS-Fi1 cameras.

Transduction quantification: Using the 4x objective, JPEG images were taken of the hippocampus, cerebral cortex, and cerebellum. The intensity of the light source and the exposure time were held constant. Images were imported into ImageJ for analysis. Individuals performing the analysis were blinded to the four AAV treatment groups. For each image, the areas outside of the region of interest were first masked (not included in the analysis). For the hippocampus and cerebral cortex, brain regions adjacent to these areas were excluded from the analysis. For the cerebellum, regions of the image outside of the molecular layer were excluded. The three color channels (red, green, and blue) were split into three separate 8-bit gray-scale images. Using the images from the green channel, the fraction of pixels in the image with values between 0 and a predetermined threshold were calculated. Since the histochemical stain is black, pixels within this range of values should correspond to those that cover stained portions of the section. PBS-treated controls were used to empirically set the threshold for each region to minimize the detection of background staining. Using the red channel, the fraction of pixels in the region of interest (i.e., the pixels that were not masked) was similarly determined. Dividing the fraction of pixels that were stained positively by the fraction of pixels covering the region of interest and multiplying by 100 yielded the fraction of the region of interest that was GFP+. For the cerebral cortex and hippocampus, four images were analyzed per animal taken evenly from the left and right sides of the brain to average out differences between the injected and uninjected sides. Similarly, six images of the cerebellum were analyzed for each animal (two right, two center, two left). Differences between treatment groups were determined by two tailed t-test.

Example 2

Transduction Biodistribution

To determine what doses might be used clinically, two main limiting factors were considered: viral titer and the volume that can safely be delivered in a reasonable amount of time. Viral titers of clinical grade vector generally range from $10^{13}$-$10^{14}$ vector genomes (vg)/ml. We estimate that 5-10% of the CSF volume can be delivered in a single bolus ICV injection, which corresponds to approximately 8-16 ml in an adult. Based on these estimates, the maximum adult ICV dose would be ~$10^{15}$ vg. Scaling the dose down based on the rat CSF volume, this dose corresponds to ~$3\times10^{12}$ vg in an adult rat. Since this dose represents the maximum under ideal conditions, the highest dose tested in this study was one-third of this maximum.

Adult Sprague-Dawley rats received a unilateral injection of scAAV9-GFP into the lateral ventricle and were sacrificed three weeks later. Three doses were evaluated: 3.1 ul (low dose, $3.7\times10^{10}$ vg), 15.5 ul (medium dose, $1.9\times10^{11}$ vg), and 77.5 ul (high dose, $9.3\times10^{11}$ vg). In addition, a fourth cohort was included that used the lowest dose of virus ($3.7\times10^{10}$ vg) delivered at the highest volume (77.5 ul) to account for differences in delivery volume (low dose/high volume). Representative images of the brains of high dose-treated rats stained for GFP are presented in FIG. 1. Two types of distribution were apparent at low magnification. In the cerebral cortex and cerebellum, the cells were evenly distributed across these regions. Qualitative analysis revealed similar GFP expression in the injected and uninjected hemispheres with the exception of the area adjacent to the injection track, which showed a high degree of GFP expression. In contrast, limbic regions, such as the hippocampus and the striatum, exhibited different transduction patterns between the two sides of the brain following unilateral injection into the lateral ventricle. Sections of cervical spinal cord stained positively for GFP, particularly in the high dose group (FIG. 1c). However, there was little evidence of transduction of cell bodies in the ventral gray matter. Instead, most of the staining appeared to be axonal projections from neurons that lie outside of the spinal cord.

Figure 2B:
Figure 2C:
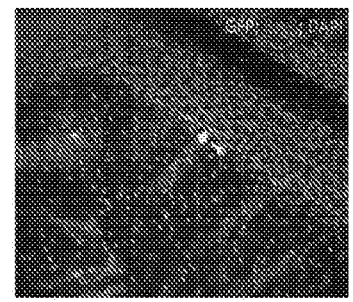
Figure 2D:
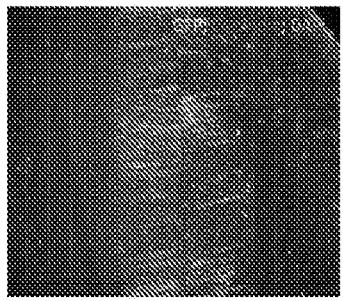
Figure 2E:
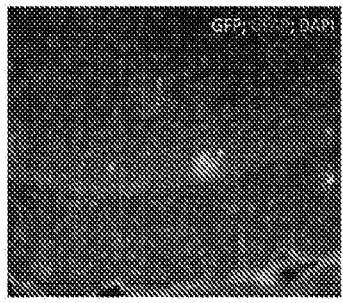
Figure 2F:
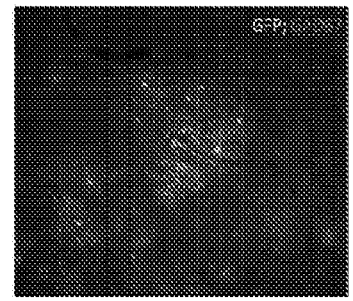
Figure 2G:
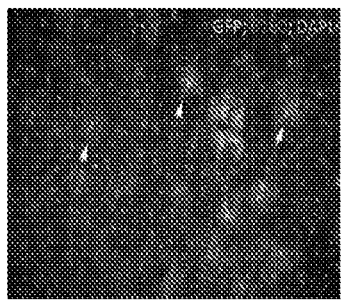

Both neuronal and glial cells were transduced with ICV delivery. Since the vector was delivered to the lateral ventricles, we first looked for transduction in the choroid plexus and the ependymal cell layer. There were many GFP+ cells in both structures (FIG. 2a). Neurons were also transduced. Staining for GFP and NeuN, a neuronal nuclei marker, colabeled cells in both the cerebral cortex and the granular layers of the hippocampus (FIG. 2b). Although neurons were transduced throughout the cerebral cortex, GAD67-expressing GABAergic neurons were not transduced (FIG. 2f). In the cerebellum, Fox2, a nuclei marker that labels Purkinje cells, colocalized with GFP staining, indicating transduction of this cell type (FIG. 2c). These GFP+ cells also stained positively for calbindin, which is expressed by several types of neurons, including Purkinje cells (FIG. 2d).(13) Many cells with an astrocytic morphology were transduced. However, no colocalization of GFAP and GFP was observed (FIG. 2e), except in close proximity to the injection track. However, S100β, another marker for astrocytes, did colocalize with these GFP+ cells, indicating astrocyte transduction (FIG. 2g).

Example 3

Transduction Efficiency in the Brain

Figure 3A:
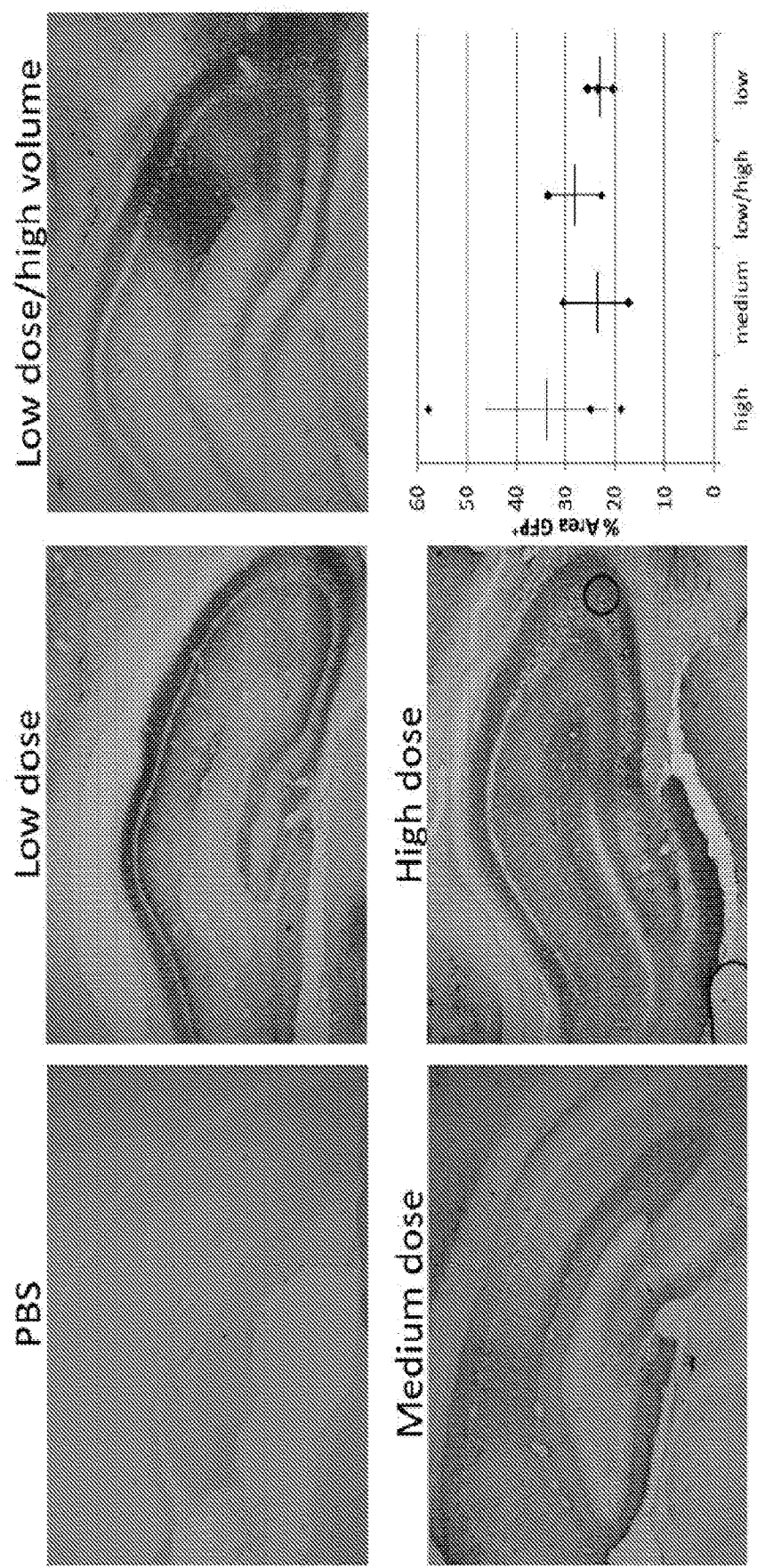
FIGS. 3a-3c. scAAV9 transduction distribution. Transduction was quantified in three brain regions [(a) hippocampus, (b) cerebral cortex, and (c) cerebellum] in five treatment groups (PBS controls, low dose, low dose/high volume, medium dose, and high dose). Each group consisted of three animals, except for the medium dose which had two. Individual animals are plotted on the graphs. The horizontal bars represent the average for each group and the error bars indicated the SEM. There was a general trend towards greater transduction with increasing dose. Increasing the injection volume did not seem to play a major role in the distribution of transduction. For the cerebral cortex and cerebellum, the medium and high dose groups were significantly different than the low dose and low dose/high volume groups ($p<0.05$).
Figure 3B:
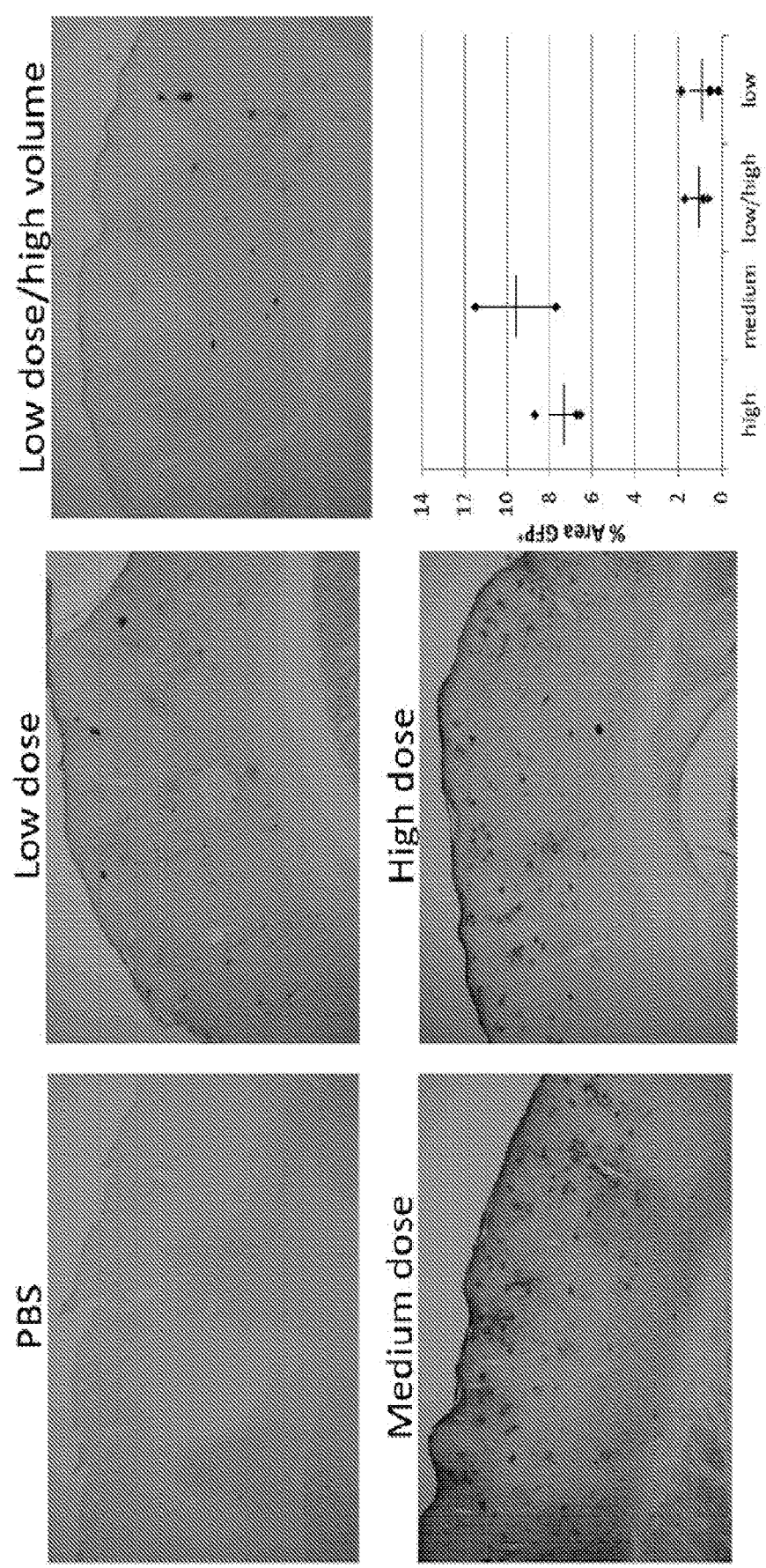
Figure 3C:
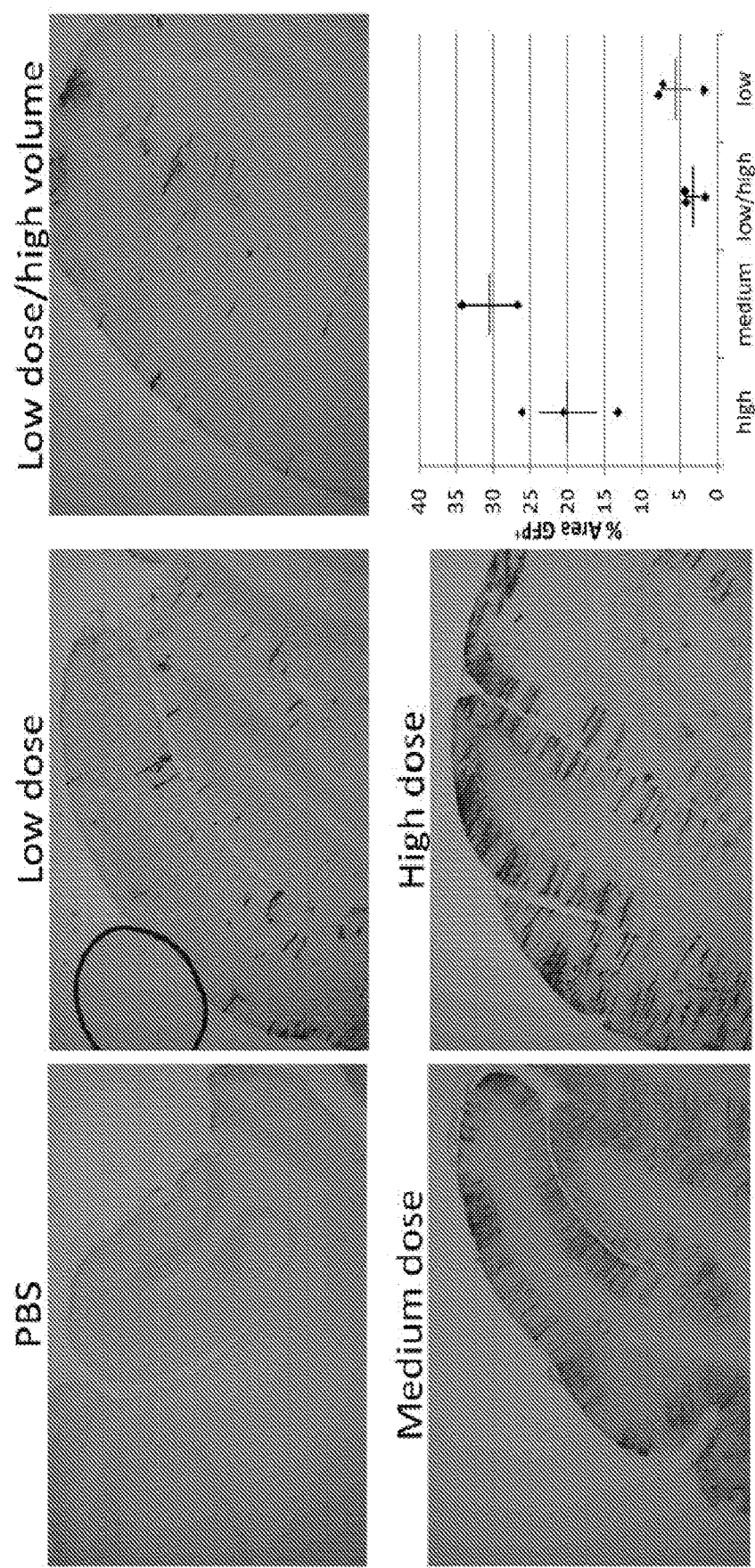
Figure 4A:
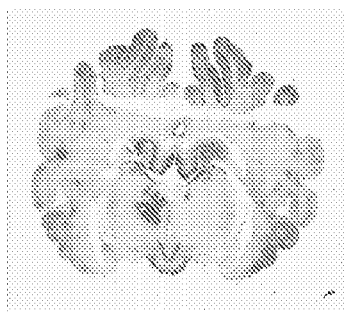
FIGS. 4a-4f. scAAV9 transduction in the pig. Three weeks following ICV injection of scAAV9-GFP into one lateral ventricle, the brain was harvested, sectioned, and stained for GFP (brown stain). Consistent with the observations in the rat, substantial transduction was observed in the (a) hippocampus, cerebral cortex, and (b) cerebellum. The brain of an untreated pig shows no staining for GFP (c). Photomicrographs taken at higher magnification are shown for (d) cerebral cortex, (e) hippocampus, and (f) cerebellum. In (d) arrows indicate examples of cells with neuronal morphology. Arrowheads indicate examples of cells exhibiting the morphology of astrocytes. The pattern of neuronal and glial transduction, based on morphology, is similar to what was seen in the rat. Scale bars are 100 um in (d) and (f) and 500 um in (e).
Figure 4B:
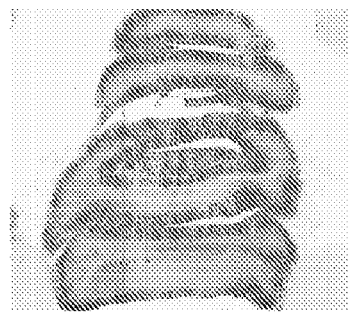
Figure 4C:
Figure 4D:
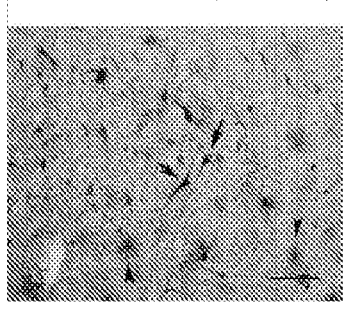
Figure 4E:
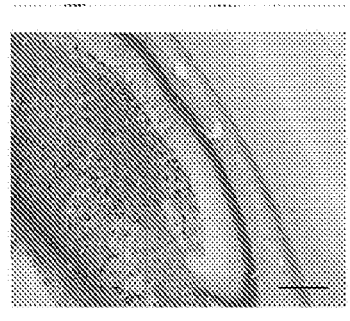
Figure 4F:
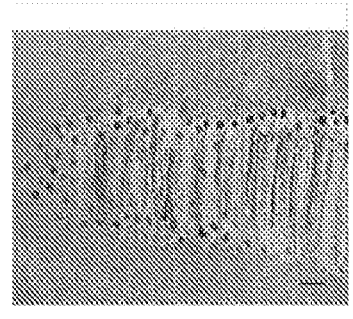

The GFP+ area was measured in three brain regions: cerebral cortex, hippocampus, and cerebellum (FIG. 3). Increasing scAAV9 dose generally led to increased transduction in all three brain regions. In the hippocampus 25% to 35% of the area was GFP+, much of the staining occurring outside of the granular layers. In the cerebellum GFP+ cells accounted 5% to 32% of the area of the molecular layer, predominantly from the transduction of Purkinje neurons. The cerebral cortex had the lowest level of transduction of the three regions quantified, with 1% to 10% of the area GFP+.

Example 4

Non-CNS Transduction

To determine if scAAV9 escaped to the periphery following ICV injection, liver samples were stained for GFP. Very few GFP cells were identified (data not shown, one positive cell in 18 cm² of tissue evaluated from medium-dose rats), suggesting that the amount of scAAV9 that escaped from the CNS was small.

Example 5

Astrocyte Activation

The introduction of foreign viruses and proteins can elicit an immune response in the CNS, often presenting as astrogliosis. To look for the presence of activated astrocytes, we stained brain sections from two PBS-treated and two high dose scAAV9-treated rats for GFAP. Eight sections, taken from regions adjacent to those illustrated in FIG. 1, were evaluated per animal, four from the cerebellum and four that included the hippocampus and cerebral cortex. GFAP staining was evaluated at low magnification to look for global changes in astrocyte activation and at higher magnification in the cerebellum, hippocampus, and cerebral cortex to look for local changes. No discernible change in staining was observed in the AAV-treated animals relative to the saline-treated animals.

Example 7

ICV Injection into the Adult Pig

Three adult farm pigs received a unilateral injection of scAAV9-GFP, with doses ranging from $2.01\times10^{13}$ to $6.03\times$ $10^{13}$ vg in volumes from 1.5 to 4.5 ml. Three weeks later, the animals were euthanized. Results were similar from all three pigs. Representative sections are shown in FIG. 4. Like the rat, there is substantial transduction of the cerebral cortex, hippocampus and cerebellum. Morphologically, these cells appear similar in appearance to those found in the rat, suggesting transduction of both neurons, including Purkinje cells, and astrocytes.

A dose-escalation study of ICV scAAV9-GFP in rats was utilized to examine the biodistribution of the vector using a range of doses expected in future clinical trials, and these observations were extended to a large animal model. Unilateral ICV injection of scAAV9-GFP led to even transduction across the entire cerebral cortex and cerebellum, while a substantial variation between the two hemispheres was observed in deeper structures, such as the hippocampus (FIG. 1).

Without being bound by theory, the majority of virus reaching the cerebellum and cerebral cortex could do so by traveling through the ventricular system to the subarachnoid space and then into the tissue, while deeper structures are transduced by vector passing through the ependymal layer, perhaps through the needle track. Whatever the source of this variation, these results suggest that bilateral ICV injection may be preferable in a clinical setting. ICV-scAAV9-GFP injections into the pig mimics the transduction pattern that observed in the rat (FIGS. 1 and 4). These data suggest that the transduction pattern observed in the rat will extend into larger mammalian brains.

ICV delivery of ssAAV9 vectors has been achieved in both mouse and dog. There are two notable differences between the transduction patterns observed in these species. In mice treated at P21, the transduction profile is a primarily neuronal in nature, although there is little transduction of Purkinje neurons. Astrocytes are poorly transduced.(7) In ICV-ssAAV9-treated adult dogs, the same pattern of transduction is found.(12) In contrast, as disclosed herein, ICV-scAAV9-treated rats and pigs have substantial transduction of astrocytes as well as neurons, and there is substantial transduction of cells in the cerebellum, particularly of Purkinje neurons. Thus, the cellular tropism and distribution pattern in this study differ markedly from previously published ICV studies in other species.

ICV delivery of AAV9, either scAAV9 or ssAAV9, has not yet been conducted in primates. However, cisterna magna delivery of scAAV9-GFP has been evaluated in macaques. (14) The authors of this study reported colocalization of GFP with neuronal and astrocytic markers, and the overall pattern of transduction in the cerebral cortex and cerebellum appears similar to what we have observed in rats and pigs. One notable difference between this macaque study and our current study is that the primates also exhibit transduction of GFAP astrocytes in addition to $S100\beta^+$ astrocytes, whereas our rodent study mainly found transduction of $S100\beta^+$ astrocytes throughout the brain, with GFP colocalizing with GFAP only around the injection tract.

Differences in AAV transduction can arise from differences in dose, method of delivery, age, and species. In recent years it has become clear that astrocytes are not a monolithic collection of cells. GFAP, generally used as a marker of astrocytes, is not immunohistochemically detectable in a subpopulation of these cell.(15) In addition, different subpopulations of astrocytes respond to stimuli in different ways,(16) and the variety of subtypes of astrocytes can vary across species.(17) Without being bound by theory, the differences between primate and rat astrocytes transduction can be explained by a preference of AAV9 for a particular subpopulation of astrocytes in the rat (a subset labeled with $S510\beta$). Alternatively, it is possible that the GFAP astrocytes transduced in the primate are not present in rats.

Given their evolutionary lineages, it is unexpected that rats, pigs, and primates would exhibit one transduction pattern (a mixture of neuronal and astrocytic transduction, high levels of cerebellar transduction) for AAV9, while mice and dogs would have another (neuronal transduction, poor cerebellar transduction). In examining the previous studies more closely, we identified one variable that correlated with the transduction pattern. Our study and the primate study (14) utilized scAAV9, whereas the mouse study (7) and the dog study (12) employed ssAAV9. scAAV vectors outperform ssAAV vectors by bypassing the need for second-strand synthesis.(18-22) This leads to increased numbers of cells being transduced, faster transgene expression, and higher levels of transgene produced. However, there have been no previous reports of ssAAV and scAAV vectors of the same serotype exhibiting different cellular tropisms. The differences observed above suggest that Purkinje neurons and astrocytes are less amenable to targeting by ssAAV9 vectors when compared to scAAV9 vectors. This represents a potential barrier for therapies using ssAAV to target these cell types.

Without being bound by theory, an explanation for this difference is that these cell types exhibit substantially lower efficiencies for second-strand synthesis relative to cortical neurons, reducing the probability that a ssAAV vector will reach a transcriptionally active state. This could point to differences in DNA repair pathways between these cell types that might contribute to Purkinje cells being more susceptible to degeneration in certain diseases.

The delivery of a foreign protein, be it simply a marker or a therapeutic gene (in the case of individuals with two null mutations), carries with it the risk of an adaptive immune response against the protein which can in turn cause loss of transduced cells. Astrocytes, in particular, can serve as antigen-presenting cells.(23) Therefore, the transduction of $S100\beta^+$ astrocytes seen after scAAV9 delivery may be of concern. Indeed, Samaranch, et al., observed behavioral defects in primates three weeks after intrathecal delivery of AAV9 that correlated with loss of Purkinje neurons. Interestingly, this loss was transgene dependent. Expression of a foreign protein, GFP, led to behavioral abnormalities, whereas expression of a self-recognized protein, hAADC, had little or no adverse effects.(24) No overt behavioral changes were observed in the rats used in the disclosed studies, and staining for GFAP did not reveal signs of astrogliosis. However, the highest dose that we used was somewhat lower than the dose used in the primate study by Samaranch et al. The delivery method was also different (ICV vs. cistern magna), although both studies investigated delivery of virus to the CSF. Immunosuppression may be required in the clinical setting.(3)

A number of disorders are good candidates for ICV AAV9-mediated therapies, such as, but not limited to, lysosomal storage diseases. Most of these disorders are due to deficiencies in a single acid hydrolase.(25) Although these enzymes are essentially needed in every cell, they can be secreted from transduced cells and taken up by nearby deficient cells in a process known as cross-correction.(26) The widespread transduction that we have observed would seem to be ideal for the treatment of this type of disorder. Indeed, ICV AAV9 treatment of mucopolysaccharidosis IIIB mice led to substantial improvements in biochemical and histological measurements of disease as well as increased life span to normal or near-normal levels.(12) Given the high levels of Purkinje neuron transduction observed in our study, diseases affecting these cells, such as spinocerebellar ataxias, are clearly targets of ICV scAAV9-mediated gene therapy. This delivery route would avoid direct injection into the parenchyma and should be safer.(27, 28).

Example 8

REFERENCES

1. Gray S J, Nagabhushan Kalburgi S, McCown T J, Jude Samulski R. Global CNS gene delivery and evasion of anti-AAV-neutralizing antibodies by intrathecal AAV administration in non-human primates. Gene Therapy 2013; 20:450-459.
Research Support, Non-U.S. Gov't]. 2013 April; 20(4): 450-9.
2. Mingozzi F, High K A. Immune responses to AAV vectors: overcoming barriers to successful gene therapy. Blood. 2013 Jul. 4; 122(1):23-36.
3. Ellinwood N M, Ausseil J, Desmaris N, Bigou S, Liu S, Jens J K, et al. Safe, efficient, and reproducible gene therapy of the brain in the dog models of Sanfilippo and Hurler syndromes. Mol Ther. 2011 February; 19(2):251-9.
4. Dayton R D, Wang D B, Klein R L. The advent of AAV9 expands applications for brain and spinal cord gene delivery. Expert Opin Biol Ther. 2012 June; 12(6):757-66.
5. McLean J R, Smith G A, Rocha E M, Hayes M A, Beagan J A, Hallett P J, et al. Widespread neuron-specific transgene expression in brain and spinal cord following synapsin promoter-driven AAV9 neonatal intracerebroventricular injection. Neurosci Lett. 2014 Jul. 25; 576:73-8.
6. Levites Y, Jansen K, Smithson L A, Dakin R, Holloway V M, Das P, et al. Intracranial adeno-associated virus-mediated delivery of anti-pan amyloid beta, amyloid beta40, and amyloid beta42 single-chain variable fragments attenuates plaque pathology in amyloid precursor protein mice. J Neurosci. 2006 Nov. 15; 26(46):11923-8.
7. Gholizadeh S, Tharmalingam S, Macaldaz M E, Hampson D R. Transduction of the central nervous system after intracerebroventricular injection of adeno-associated viral vectors in neonatal and juvenile mice. Hum Gene Ther Methods. 2013 August; 24(4):205-13.
8. Dirren E, Towne C L, Setola V, Redmond D E, Jr., Schneider B L, Aebischer P. Intracerebroventricular injection of adeno-associated virus 6 and 9 vectors for cell type-specific transgene expression in the spinal cord. Hum Gene Ther. 2014 February; 25(2):109-20.
9. Chakrabarty P, Rosario A, Cruz P, Siemienski Z, Ceballos-Diaz C, Crosby K, et al. Capsid serotype and timing of injection determines AAV transduction in the neonatal mice brain. PLoS One. 2013; 8(6):e67680.
10. Broekman M L, Baek R C, Comer L A, Fernandez J L, Seyfried T N, Sena-Esteves M. Complete correction of enzymatic deficiency and neurochemistry in the GM1-gangliosidosis mouse brain by neonatal adeno-associated virus-mediated gene delivery. Mol Ther. 2007 January; 15(1):30-7.
11. Nathwani A C, Tuddenham E G, Rangarajan S, Rosales C, McIntosh J, Linch D C, et al. Adenovirus-associated virus vector-mediated gene transfer in hemophilia B. N Engl J Med. 2011 Dec. 22; 365(25):2357-65.
12. Haurigot V, Marco S, Ribera A, Garcia M, Ruzo A, Villacampa P, et al. Whole body correction of mucopolysaccharidosis IIIA by intracerebrospinal fluid gene therapy. J Clin Invest. 2013 Jul. 1.
13. Bastianelli E. Distribution of calcium-binding proteins in the cerebellum. Cerebellum. 2003; 2(4):242-62.
14. Samaranch L, Salegio E A, San Sebastian W, Kells A P, Foust K D, Bringas J R, et al. Adeno-associated virus serotype 9 transduction in the central nervous system of nonhuman primates. Hum Gene Ther. 2012 April; 23(4): 382-9.
15. Sofroniew M V, Vinters H V. Astrocytes: biology and pathology. Acta Neuropathol. 2010 January; 119(1):7-35.
16. Benesova J, Hock M, Butenko O, Prajerova I, Anderova M, Chvatal A. Quantification of astrocyte volume changes during ischemia in situ reveals two populations of astrocytes in the cortex of GFAP/EGFP mice. J Neurosci Res. 2009 January; 87(1):96-111.
17. Oberheim N A, Takano T, Han X, He W, Lin J H, Wang F, et al. Uniquely hominid features of adult human astrocytes. J Neurosci. 2009 Mar. 11; 29(10):3276-87.
18. McCarty D M. Self-complementary AAV vectors; advances and applications. Mol Ther. 2008 October; 16(10): 1648-56.
19. McCarty D M, Monahan P E, Samulski R J. Self-complementary recombinant adeno-associated virus (scAAV) vectors promote efficient transduction independently of DNA synthesis. Gene Ther. 2001 August; 8(16): 1248-54.
20. McCarty D M, Fu H, Monahan P E, Toulson C E, Naik P, Samulski R J. Adeno-associated virus terminal repeat (TR) mutant generates self-complementary vectors to overcome the rate-limiting step to transduction in vivo. Gene Ther. 2003 December; 10(26):2112-8.
21. Wang Z, Ma H I, Li J, Sun L, Zhang J, Xiao X. Rapid and highly efficient transduction by double-stranded adeno-associated virus vectors in vitro and in vivo. Gene Ther. 2003 December; 10(26):2105-11.
22. Nathwani A C, Gray J T, Ng C Y, Zhou J, Spence Y, Waddington S N, et al. Self-complementary adeno-associated virus vectors containing a novel liver-specific human factor IX expression cassette enable highly efficient transduction of murine and nonhuman primate liver. Blood. 2006 Apr. 1; 107(7):2653-61.
23. Fontana A, Fierz W, Wekerle H. Astrocytes present myelin basic protein to encephalitogenic T-cell lines. Nature. 1984 Jan. 19-25;307(5948):273-6.
24. Samaranch L, San Sebastian W, Kells A P, Salegio E A, Heller G, Bringas J R, et al. AAV9-mediated expression of a non-self protein in nonhuman primate central nervous system triggers widespread neuroinflammation driven by antigen-presenting cell transduction. Mol Ther. 2014 February; 22(2):329-37.
25. Hollak C E, Wijburg F A. Treatment of lysosomal storage disorders: successes and challenges. J Inherit Metab Dis. 2014 July; 37(4):587-98.
26. Sands M S, Davidson B L. Gene therapy for lysosomal storage diseases. Mol Ther. 2006 May; 13(5):839-49.
27. Xia H, Mao Q, Eliason S L, Harper S Q, Martins I H, Orr H T, et al. RNAi suppresses polyglutamine-induced neurodegeneration in a model of spinocerebellar ataxia. Nat Med. 2004 August; 10(8):816-20.
28. Costa Mdo C, Luna-Cancalon K, Fischer S, Ashraf N S, Ouyang M, Dharia R M, et al. Toward RNAi therapy for the polyglutamine disease Machado-Joseph disease. Mol Ther. 2013 October; 21(10):1898-908.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of treating a human subject diagnosed with a CNS disorder, comprising:
administering by injection into the cerebrospinal fluid to the human subject via an intracerebroventricular, intrathecal cisternal, or intrathecal lumbar route, an effective amount of a scAAV9 encoding a therapeutic protein at a flat dose of about $1.2 \times 10^{14}$ GC, wherein the CNS disorder is Spinal Muscular Atrophy, the therapeutic protein is SMN1, and the human subject is 3 to 12 years old,
thereby treating the CNS disorder and alleviating a symptom of the CNS disorder in the human subject.

2. A method of treating a human subject diagnosed with a CNS disorder, comprising:
administering by injection into the cerebrospinal fluid to the human subject via an intracerebroventricular, intrathecal cisternal, or intrathecal lumbar route, an effective amount of a scAAV9 encoding a therapeutic protein at a flat dose of about $1.2 \times 10^{14}$ GC, wherein the CNS disorder is Spinal Muscular Atrophy, the therapeutic protein is SMN1, and the human subject is 9 to 36 months old, thereby treating the CNS disorder and alleviating a symptom of the CNS disorder in the human subject.

3. The method of claim 1, further comprising administering to the subject a therapeutically effective amount of an immunosuppressive agent.

4. The method of claim 3, wherein the immunosuppressive agent diminishes the activity of cytotoxic T cells.

5. The method of claim 3, wherein the immunosuppressive agent reduces encephalitis.

6. The method of claim 3, wherein the immunosuppressive agent is a non-steroidal anti-inflammatory agent.

7. The method of claim 1, wherein the method reduces the risk of encephalitis in the subject.

8. The method of claim 1, wherein the scAAV9 transduces cells in a hippocampus, cerebellum and cerebral cortex of the human subject.

9. The method of claim 2, further comprising administering to the subject a therapeutically effective amount of an immunosuppressive agent.

10. The method of claim 9, wherein the immunosuppressive agent diminishes the activity of cytotoxic T cells.

11. The method of claim 9, wherein the immunosuppressive agent reduces encephalitis.

12. The method of claim 9, wherein the immunosuppressive agent is a non-steroidal anti-inflammatory agent.

13. The method of claim 2, wherein the method reduces the risk of encephalitis in the subject.

14. The method of claim 2, wherein the scAAV9 transduces cells in a hippocampus, cerebellum and cerebral cortex of the human subject.

* * * * *